US010342916B2

(12) United States Patent
Small et al.

(10) Patent No.: US 10,342,916 B2
(45) Date of Patent: Jul. 9, 2019

(54) SINGLE-HEAD POWER INJECTOR WITH CONTRAST MEDIA LEAKAGE MANAGEMENT

(71) Applicant: Liebel-Flarsheim Company LLC, Cincinnati, OH (US)

(72) Inventors: James R. Small, Beavercreek, OH (US); Robert J. McGraw, Cincinnati, OH (US)

(73) Assignee: LIEBEL-FLARSHEIM COMPANY LLC, Cincinnati, OH (US)

( * ) Notice: Subject to any disclaimer, the term of this patent is extended or adjusted under 35 U.S.C. 154(b) by 0 days.

(21) Appl. No.: 15/551,558

(22) PCT Filed: Mar. 2, 2016

(86) PCT No.: PCT/US2016/020494
§ 371 (c)(1),
(2) Date: Aug. 16, 2017

(87) PCT Pub. No.: WO2016/141087
PCT Pub. Date: Sep. 9, 2016

(65) Prior Publication Data
US 2018/0021505 A1   Jan. 25, 2018

Related U.S. Application Data

(60) Provisional application No. 62/127,692, filed on Mar. 3, 2015.

(51) Int. Cl.
*A61M 5/00* (2006.01)
*A61M 5/31* (2006.01)
*A61M 5/145* (2006.01)

(52) U.S. Cl.
CPC .......... *A61M 5/007* (2013.01); *A61M 5/1456* (2013.01); *A61M 5/14546* (2013.01);
(Continued)

(58) Field of Classification Search
CPC ...... A61M 5/007; A61M 5/31; A61M 5/1456; A61M 5/14546; A61M 2205/505;
(Continued)

(56) References Cited

U.S. PATENT DOCUMENTS 4,006,736 A    2/1977 Kranys et al.
2002/0128594 A1* 9/2002 Das .................... A61M 5/1456
                                                  604/67
(Continued)

FOREIGN PATENT DOCUMENTS

WO    2010117923 A1    10/2010
WO    2013126318 A1    8/2013

OTHER PUBLICATIONS

International Search Report and Written Opinion of the International Searching Authority (Forms PCT/ISA/220, PCT/ISA/210 and PCT/ISA/237), dated Aug. 26, 2016, for International Application No. PCT/US2016/020494.

*Primary Examiner* — Lauren P Farrar
(74) *Attorney, Agent, or Firm* — Marsh Fischmann & Breyfogle LLP

(57) ABSTRACT

A power injector (200) is disclosed that includes a number of features to address leakage of contrast media from a syringe that may occur while operating the power injector (200), for instance when loading fluid into a syringe after being installed on a powerhead (210) of the injector (200) and/or when purging air from such a syringe. One or more drainage channels (240) may be incorporated on a faceplate mounting (234) which in turn receives a faceplate (310), which in turn receives a syringe. A cover assembly (260) may utilize a form-in-place gasket (274) between its top cover (262) and its bottom cover (290). A bezel (330) includes an overlay (334) that is disposed over a touch screen display (380) that is aligned with a display aperture (Continued)

(264) through the top cover (262), and the bezel (330) may include a gasket (350) to seal against the top cover (262).

30 Claims, 30 Drawing Sheets

(52) U.S. Cl.
CPC ..... *A61M 5/31* (2013.01); *A61M 2005/14553* (2013.01); *A61M 2005/3101* (2013.01); *A61M 2005/3125* (2013.01); *A61M 2205/505* (2013.01)

(58) Field of Classification Search
CPC .. A61M 2005/3125; A61M 2005/3101; A61M 2005/14553
See application file for complete search history.

(56) References Cited

U.S. PATENT DOCUMENTS

| | | | |
|---|---|---|---|
| 2004/0133153 A1* | 7/2004 | Trocki | A61M 5/14546 604/93.01 |
| 2006/0079768 A1* | 4/2006 | Small | A61M 5/14546 600/432 |
| 2010/0228222 A1 | 9/2010 | Williams et al. | |
| 2011/0160652 A1* | 6/2011 | Yodfat | A61M 5/1413 604/66 |

* cited by examiner

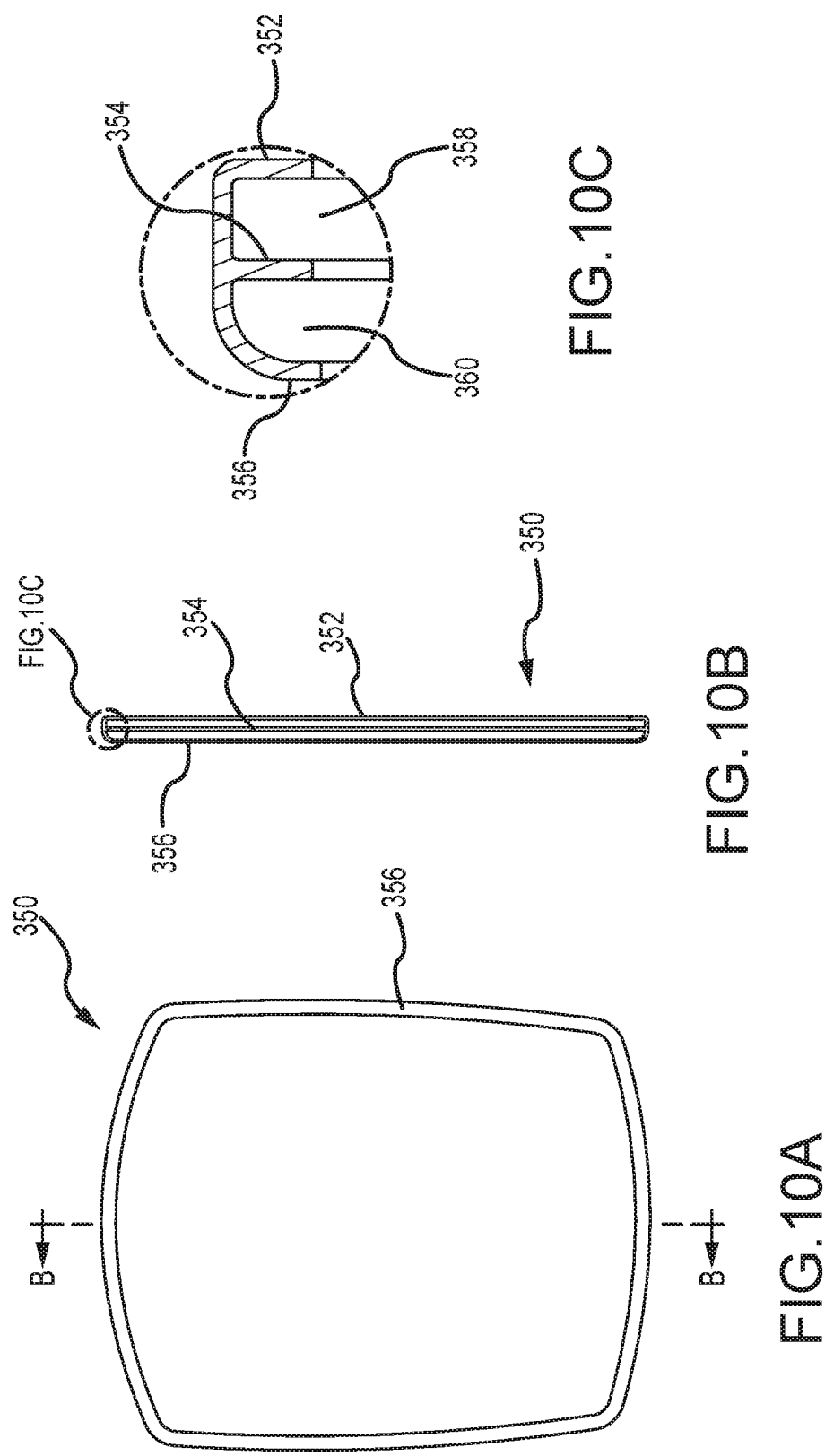

SINGLE-HEAD POWER INJECTOR WITH CONTRAST MEDIA LEAKAGE MANAGEMENT

CROSS-REFERENCE TO RELATED APPLICATIONS

This patent application is a U.S. National Stage of International Application No. PCT/US2016/020494 (co-pending), filed on Mar. 2, 2016, which claims the benefit of U.S. Provisional Patent Application Ser. No. 62/127,692, filed on Mar. 3, 2015, and the entire disclosure of which is hereby incorporated by reference herein.

FIELD OF THE INVENTION

The present invention generally relates to power injectors and, more particularly, to addressing leakage of contrast media from a syringe during operation of the power injector.

BACKGROUND

Various medical procedures require that one or more medical fluids be injected into a patient. For example, medical imaging procedures oftentimes involve the injection of contrast media into a patient, possibly along with saline and/or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

SUMMARY

A first aspect of the present invention pertains to a power injector having a first drive source, a powerhead, and a syringe mount that is installed on or otherwise incorporated by the powerhead. The powerhead includes a drive ram that is moved or advanced along a reference axis in at least one direction through operation of the first drive source. The powerhead further includes a front plate, where the front plate includes at least one drainage channel. This front plate also includes a ram aperture that is aligned with the drive ram.

A second aspect of the present invention pertains to a power injector having a first drive source, a powerhead, a syringe mount that is installed on or otherwise incorporated by the powerhead, and a cover assembly. The powerhead includes a drive ram that is moved or advanced along a reference axis in at least one direction through operation of the first drive source. The cover assembly includes a top cover that is detachably connected with a bottom cover. One of the top cover or the bottom cover includes a form-in-place gasket that seals against the other cover.

A third aspect of the present invention pertains to a power injector having a first drive source, a powerhead, a syringe mount that is installed on or otherwise incorporated by the powerhead, a touch screen display that is incorporated by the powerhead, a bezel, and a cover assembly. The powerhead includes a drive ram that is moved or advanced along a reference axis in at least one direction through operation of the first drive source. The bezel includes an overlay that is disposed over the touch screen display. A bezel gasket is disposed about a perimeter of the bezel and engages the cover assembly to define a seal between the cover assembly and the bezel.

A fourth aspect of the present invention pertains to a power injector having a first drive source, a powerhead, a syringe mount that is installed on or otherwise incorporated by the powerhead, and a cover assembly. The powerhead includes a drive ram that is moved or advanced along a reference axis in at least one direction through operation of the first drive source. A knob is disposed exteriorly of the cover assembly, and extends through an aperture of the cover assembly for interconnection with the drive ram. An annular rim is disposed about this aperture.

A number of feature refinements and additional features are separately applicable to each of above-noted first, second, and third, and fourth aspects of the present invention. These feature refinements and additional features may be used individually or in any combination in relation to each of the first, second, third, and fourth aspects. By way of initial summary, each of these aspects may be used in combination with any one of more of the other aspects.

The powerhead may include a front plate (e.g., attached to a front end of the powerhead in any appropriate manner, for instance detachably using one or more fasteners), where this front plate includes at least one drainage channel. This front plate includes a ram aperture that is aligned with the drive ram. One or more of the drainage channels incorporated by the front plate may be in accordance with any one or more of the following, including where a given drainage channel: 1) extends from the ram aperture to a bottom or lower end of the front plate; 2) is in the form of an open, concave structure; 3) projects or faces away from the powerhead; and 4) projects or faces in a direction in which the drive ram moves for a fluid discharge operation.

The noted front plate may include any appropriate number of drainage channels, and each of which may be disposed in any appropriate orientation. One embodiment has the front plate including first and second drainage channels. The first and second drainage channels may be oriented as the mirror image of one another. The first and second drainage channels may diverge away from one another as they proceed away from the ram aperture and toward a perimeter of the front plate.

The front plate may be in the form of or include a faceplate mounting (e.g., a protrusion), where the power injector may then include a faceplate that is detachably mounted to this faceplate mounting. The faceplate mounting, alone or in combination with the faceplate, may be characterized as a syringe mount for the power injector (e.g., to accommodate a syringe being installed on the powerhead). One or more of the drainage channels may be located between the faceplate and the front plate (e.g., the faceplate may be disposed over the drainage channel(s) of the front plate). The front plate may include a first surface and a front face that are disposed in different orientations, where the first surface is located in proximity to the ram aperture, and where the drainage channel is formed on the front face of the front plate. The front face may be a flat surface and/or may be the leading portion of a protrusion on the front plate (e.g., such a protrusion accommodating installation of a faceplate on the injector). The first surface may be in accordance with any one or more of the following, including where the first surface: 1) is arcuate or curved; 2) is disposed at least generally parallel with the reference axis along which the drive ram moves (including where the front face is disposed within a plane that is at least generally perpendicular to this reference axis); 3) is disposed below or underneath the drive ram when the drive ram has extended through the ram aperture of the front plate; and 4) extends along only a portion of a perimeter of the ram aperture, for instance less than 180° of the perimeter of the ram aperture.

The noted first surface may be characterized as extending away from a base of the front plate. For instance, the first surface may extend away from the base of the front plate in a direction that the drive ram moves when it is extending further beyond the powerhead for a fluid discharge operation. The first surface may then be characterized as a ledge or the like for the collection of contrast media that may spill. Contrast media that collects on the first surface may be directed away from the powerhead by flowing through one or more of the noted drainage channels on the front face of the front plate.

The power injector may include a cover assembly (e.g., for enclosing the powerhead; defining a housing for the powerhead) having a top cover that may be detachably connected with a bottom cover in any appropriate manner. One of the top cover or the bottom cover may include a form-in-place gasket that seals against the other cover. In one embodiment it is the top cover that includes the form-in-place gasket. The form-in-in-place gasket may be anchored to the relevant cover in any appropriate manner (e.g., using one or more adhesives) and may seal against the other cover. That is, the form-in-place gasket may be physically associated with a relevant one of the covers.

There may be an interface between the top cover and the bottom cover. In the case where the noted top cover incorporates a form-in-place gasket, the noted form-in-place gasket may engage the bottom cover throughout an entirety of this interface. The lower portion of the top cover may be disposed over an upper portion of the bottom cover. Stated another way, an overlap may exist between the top cover and the bottom cover, where the top cover is disposed beyond the bottom cover for the overlap. The noted form-in-place gasket may be located within this overlap, including where the form-in-place gasket extends along an entirety of a perimeter of this overlap. Consider the case where the top cover includes a lower end. The form-in-place gasket may be recessed relative to this lower end (e.g., the portion of the top cover extending from the form-in-place gasket to the lower end of the top cover may define the noted overlapping portion of the top cover).

Further features pertain to a cover assembly for the power injector. A knob may be disposed exteriorly of this cover assembly, and may extend through an aperture of the cover assembly for interconnection with the drive ram (e.g., to manually control movement of the drive ram in at least one direction). An annular rim may be disposed about this aperture—the rim extends about the entire perimeter of this aperture. This particular aperture may be on a rear wall of the cover assembly (e.g., with the syringe mount being disposed opposite of this rear wall). In one embodiment the annular rim protrudes at least about 0.125 inches beyond the rear wall of the cover assembly.

A touch screen display may be incorporated by the powerhead (e.g., aligned with an aperture through a cover assembly for the power injector), and the power injector may further include a bezel. The bezel may be detachably mounted in any appropriate manner (e.g., the bezel may detachably engage at least one of a display mounting bracket or the touch screen display itself), and may include an overlay that is disposed over the touch screen display. A bezel gasket may be disposed about a perimeter of the bezel and may engage the cover assembly to define a seal between the cover assembly and the bezel. The bezel gasket may include a section that cantilevers and deflects when engaged by the cover assembly (e.g., when installing the top cover over the powerhead, and with the bezel having already been installed). In addition to providing a contrast media leakage feature, the noted configuration also allows the bezel to be replaced if its overlay becomes scratched or the like, where this overlay is for protecting the touch screen display (versus having to replace the top cover, should the top cover be configured to include an overlay to protect the touch screen display).

It should be appreciated that each of the first, second, third, and fourth aspects of the present invention may be characterized as being directed to contrast media leakage management. The noted drainage channel(s), the form-in-place gasket between the top cover and the bottom cover, the annular rim about an aperture through the cover assembly, and a gasket between a bezel and the cover assembly, individually and in any combination, may be used to reduce the potential of contrast media (e.g., spillage) adversely affecting the power injector.

Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a front plate includes "a drainage channel" alone does not mean that the front plate includes only a single drainage channel). Moreover, any failure to use phrases such as "at least one" also does not limit the corresponding feature to the singular (e.g., indicating that a front plate includes "a drainage channel" alone does not mean that the front plate includes only a single drainage channel). Use of the phrase "at least generally" or the like in relation to a particular feature encompasses the corresponding characteristic and insubstantial variations thereof (e.g., indicating that a pair of drainage channels are at least generally the mirror image of each other with regard to their respective orientations encompasses such a pair of drainage channels actually being the mirror image with regard to their respective orientations). Finally, a reference of a feature in conjunction with the phrase "in one embodiment" does not limit the use of the feature to a single embodiment.

BRIEF DESCRIPTION OF THE FIGURES

FIG. 10A is a plan view of a gasket for the bezel shown in FIGS. 9A and 9B.

FIG. 10B is a cross-sectional view of the gasket shown in FIG. 10A, taken along line B-B.

FIG. 10C is an enlarged view of the region 100 for the bezel gasket shown in FIG. 10B.

DETAILED DESCRIPTION

Figure 1:
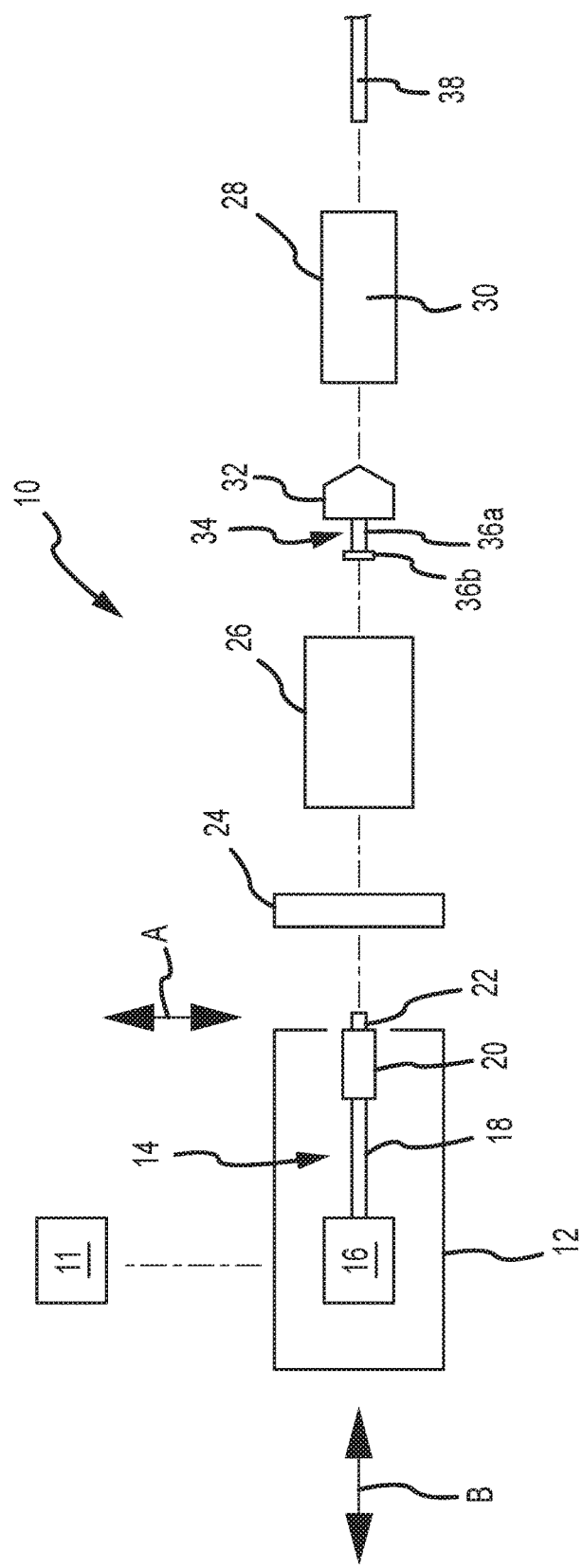
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide any of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on the powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, these components may or may not be coupled when the ram 20 advances the syringe plunger 32 to discharge fluid from the syringe 28 (e.g., the ram 20 may simply "push on" the syringe plunger coupler 34 or directly on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
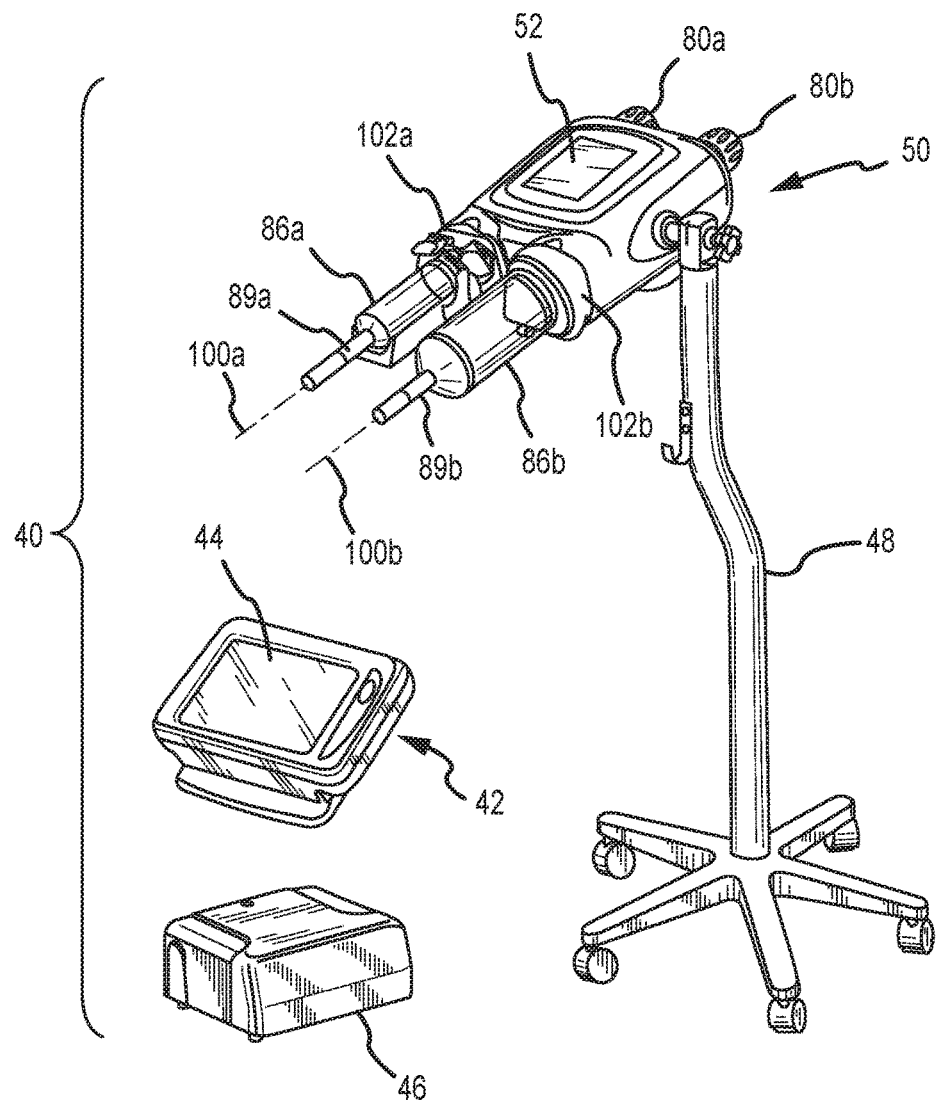
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. Two syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
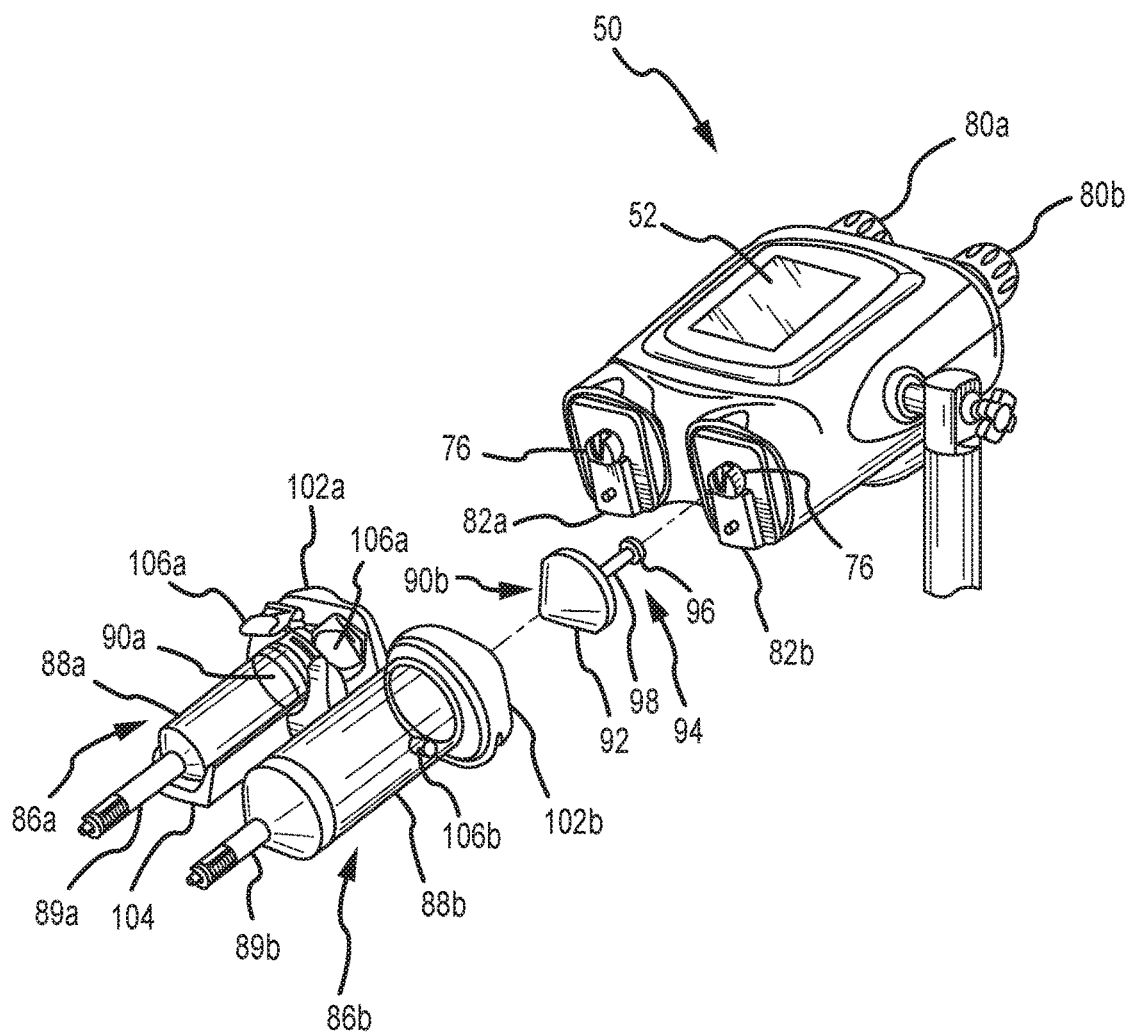
FIG. 2B is an enlarged, partially exploded, perspective view of a powerhead used by the dual-head power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 2C), which are each part of a syringe plunger drive assembly or syringe plunger driver 56 (FIG. 2C) for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 (FIG. 2C) may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74 (FIG. 2C), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 (FIG. 2C) may be moved relative to the powerhead 50 to move the syringe plunger 90b along the axis 100b (FIG. 2A). It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b.

Generally and with the syringe 86*b* being initially positioned within the faceplate 102*b*, the syringe 86*b* may be rotated along its long axis 100*b* (FIG. 2A) and relative to the faceplate 102*b*. This rotation may be realized by moving the handle 106*b*, by grasping and turning the syringe 86*b*, or both. In any case, this rotation moves/translates both the syringe 86*b* and the faceplate 102*b* at least generally within a plane that is orthogonal to the axes 100*a*, 100*b* (associated with movement of the syringe plungers 90*a*, 90*b*, respectively, and illustrated in FIG. 2A). Rotating the syringe 86*b* in one direction moves/translates the syringe 86*b* and faceplate 102*b* in an at least generally downward direction to couple the syringe plunger 90*b* with its corresponding ram coupler 76. Rotating the syringe 86*b* in the opposite direction moves/translates the syringe 86*b* and faceplate 102*b* in an at least generally upward direction to uncouple its syringe plunger 90*b* from its corresponding ram coupler 76.

As illustrated in FIG. 2B, the syringe plunger 90*b* includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90*b* and its corresponding ram coupler 76 are in a coupled state or condition. The syringe plunger 90*a* may include a similar syringe plunger coupler 94 for interfacing with its corresponding ram coupler 76.

Figure 2C:
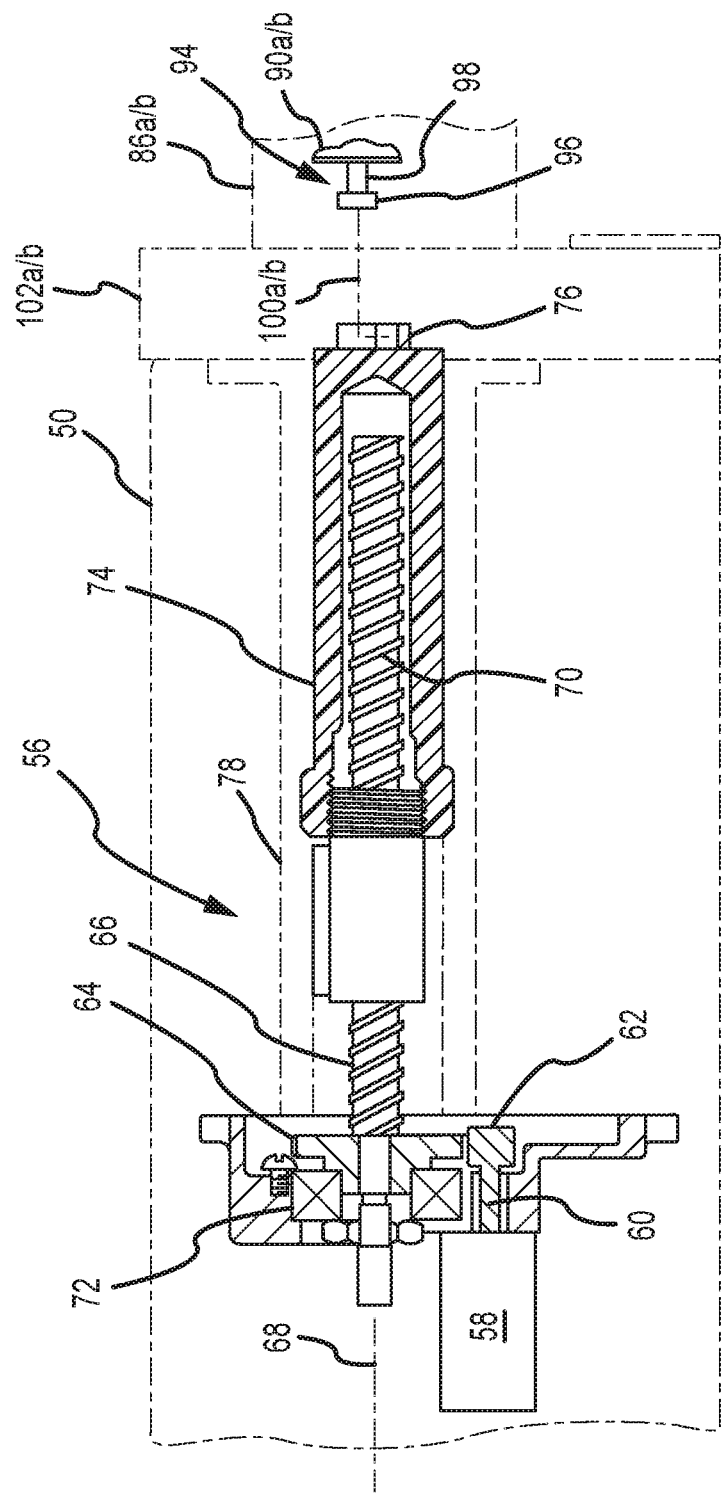
FIG. 2C is a schematic of one embodiment of a syringe plunger drive assembly used by the dual-head power injector of FIG. 2A.

The powerhead 50 is utilized to discharge fluid from the syringes 86*a*, 86*b* in the case of the power injector 40. That is, the powerhead 50 provides the motive force to discharge fluid from each of the syringes 86*a*, 86*b*. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86*a*, 86*b*. A separate syringe plunger drive assembly 56 may be incorporated into the powerhead 50 for each of the syringes 86*a*, 86*b*. In this regard and referring back to FIGS. 2A-B, the powerhead 50 may include hand-operated knobs 80*a* and 80*b* for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86*a/b*, while rotation of the drive screw 66 in the opposite direction axially advances the ram 74 along the drive screw 66 (and thereby along axis 68) away from the corresponding syringe 86*a/b*. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90*a/b* of the corresponding syringe 86*a/b*. When the ram coupler 76 and syringe plunger coupler 94 are appropriately coupled, the syringe plunger 90*a/b* moves along with ram 74. FIG. 2C illustrates a configuration where the syringe 86*a/b* may be moved along its corresponding axis 100*a/b* without being coupled to the ram 74. When the syringe 86*a/b* is moved along its corresponding axis 100*a/b* such that the head 96 of its syringe plunger 90*a/b* is aligned with the ram coupler 76, but with the axes 68 still in the offset configuration of FIG. 2C, the syringe 86*a/b* may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient) and/or any appropriate medical diagnostic and/or therapeutic application (e.g., injection of chemotherapy, pain management, etc.). Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, therapeutic fluid, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

The power injector 40 of FIGS. 2A and 2B may be referred to as a dual-head power injector 40 or as being of a dual-head configuration/design (to accommodate multiple syringes). FIGS. 3A-3F present one embodiment of a single-head power injector 200 (one that accommodates a single syringe of the type at least generally described herein). Various features that may be utilized by the power injector 200 are described in more detail in one or more of commonly assigned U.S. Pat. No. 7,507,221 (issued Mar. 24, 2009); U.S. Pat. No. 8,663,166 (issued Mar. 4, 2014); and U.S. Pat. No. 8,454,560 (issued Jun. 4, 2013), and the entire disclosure of each of these patents is hereby incorporated by reference.

The power injector 200 utilizes a powerhead 210 and a faceplate 310 (or more generally a syringe mount), where this faceplate 310 is detachably connected to the powerhead 210 in any appropriate manner and receives a single syringe for installation on the powerhead 210. The faceplate 310 may be characterized as including an end section 312 through which a syringe aperture 314 extends, and where this end section 312 is disposed adjacent to a front end 212 of the powerhead 210 when the faceplate 310 is installed on the powerhead 210. A cradle 316 extends from the end section 312 and in a direction that is away from the powerhead 210. At least part of a barrel of a syringe may be positioned on this cradle 316, and which may incorporate a heater to control the temperature of the fluid (e.g., contrast media) in such a syringe. An actuator 318 may be used to secure a syringe within the faceplate 310 and relative to the powerhead 210, for instance at least generally in accordance with the disclosure of U.S. Pat. No. 8,454,560, noted above.

The powerhead 210 may include one or more motors or other drive sources of the above-noted type (not shown, but which may be of any appropriate size, shape, configuration, and/or type) that moves a drive ram 216 (FIG. 3F) along an axis or axial path. Multiple drive source outputs may be combined in any appropriate manner to advance the common drive ram 216 for the power injector 200. Representative drive source forms for the power injector 200 include without limitation a brushed or brushless electric motor, a hydraulic motor, a pneumatic motor, a piezoelectric motor, or a stepper motor.

Operation of the drive source(s) for the power injector 200 may advance the drive ram 216 in one direction along an axis to discharge fluid from a syringe installed on the powerhead 210 via the faceplate 310, including where the drive ram 216 extends beyond the powerhead 210. Operation of the drive source(s) for the power injector 200 may advance the drive ram 216 in an opposite direction along this same axis to retract the drive ram 216, including where this retraction of the drive ram 216 accommodates loading of fluid into a syringe installed on the powerhead 210 via the faceplate 310, where this retraction of the drive ram 216 disposes the drive ram 216 entirely within the interior of the powerhead 210, or both. An end of the drive ram 216 may include a slot 218 or other appropriate connector such that movement of the drive ram 216 in one direction will advance a plunger of a syringe in the same direction as the drive ram 216, and such that movement of the drive ram 216 in a directly opposite direction will advance a plunger of a syringe in the same direction as the drive ram 216. The drive ram 216 is at least generally in accordance with the disclosure of U.S. Pat. No. 8,454,560.

The powerhead 210 may be characterized as including a front end 212 and a rear end 214 that are spaced from one another in the direction that the drive ram 216 may be advanced relative to the powerhead 210. Operation of an appropriate motor(s) or other drive source(s), for instance which may disposed within the powerhead 210, may advance the drive ram 216 relative to the powerhead 210 in each of two opposite directions along an axis and as noted. A knob 224 is located at the rear end 214 of the powerhead 210, may be manually rotated by an operator in one direction to advance the drive ram 216 along the noted axis in one direction (e.g., a fluid discharge direction), and may be manually rotated by an operator in an opposite direction to advance the drive ram 216 along the noted access in the opposite direction (e.g., a fluid loading direction).

Figure 3A:
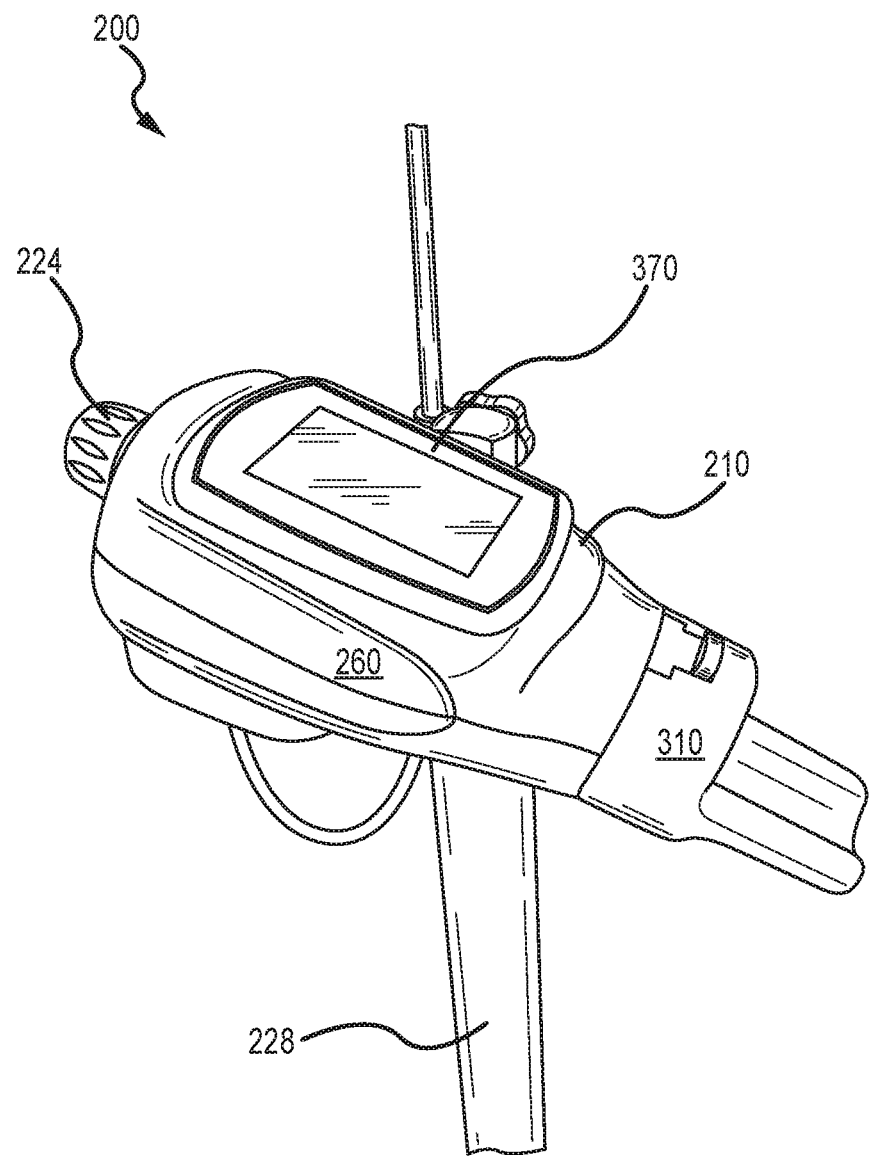
FIG. 3A is one perspective view of a top and one side of one embodiment of a single-head power injector, and with its powerhead being in a tilted down orientation.
Figure 3B:
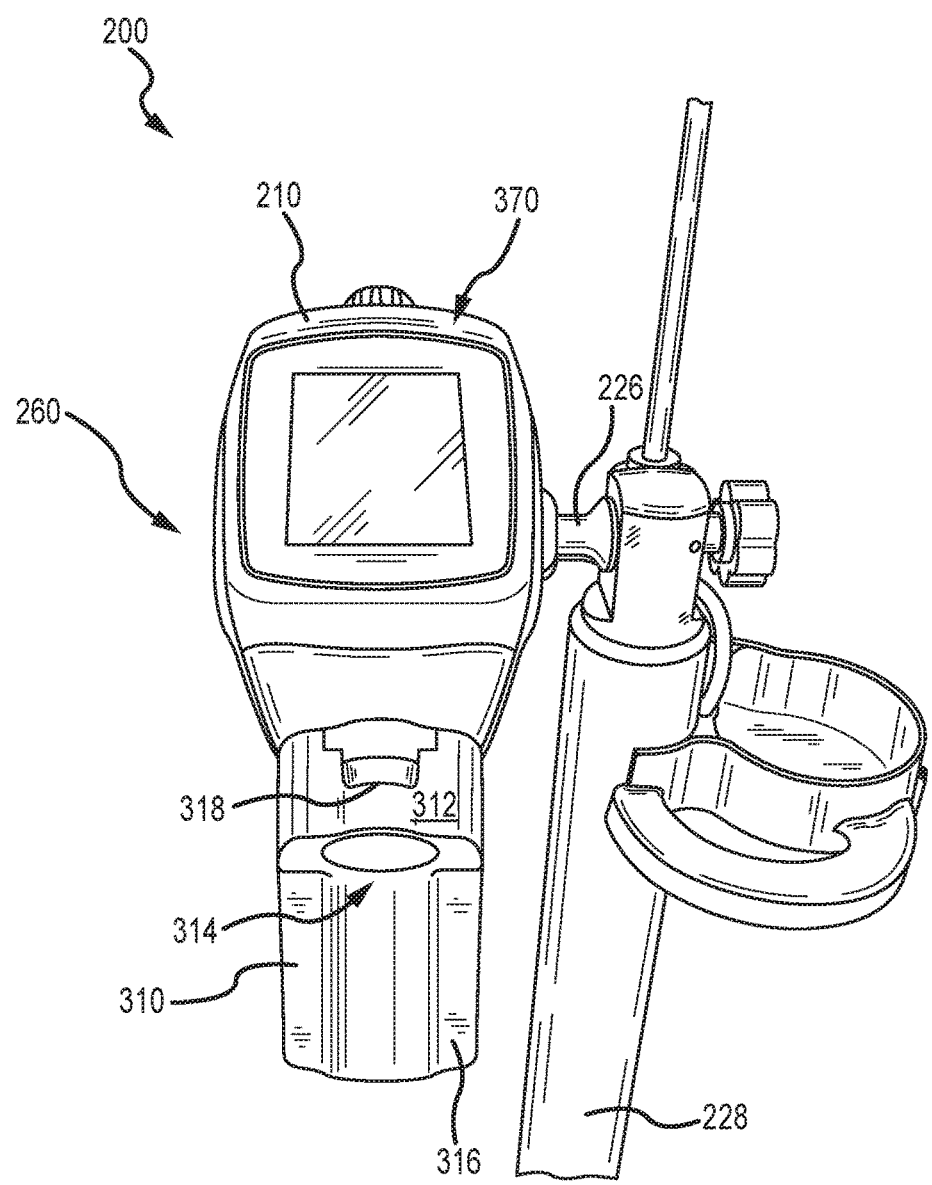
FIG. 3B is a perspective view of a top of the single-head power injector of FIG. 3A, and with its powerhead being in a tilted down orientation.
Figure 3C:
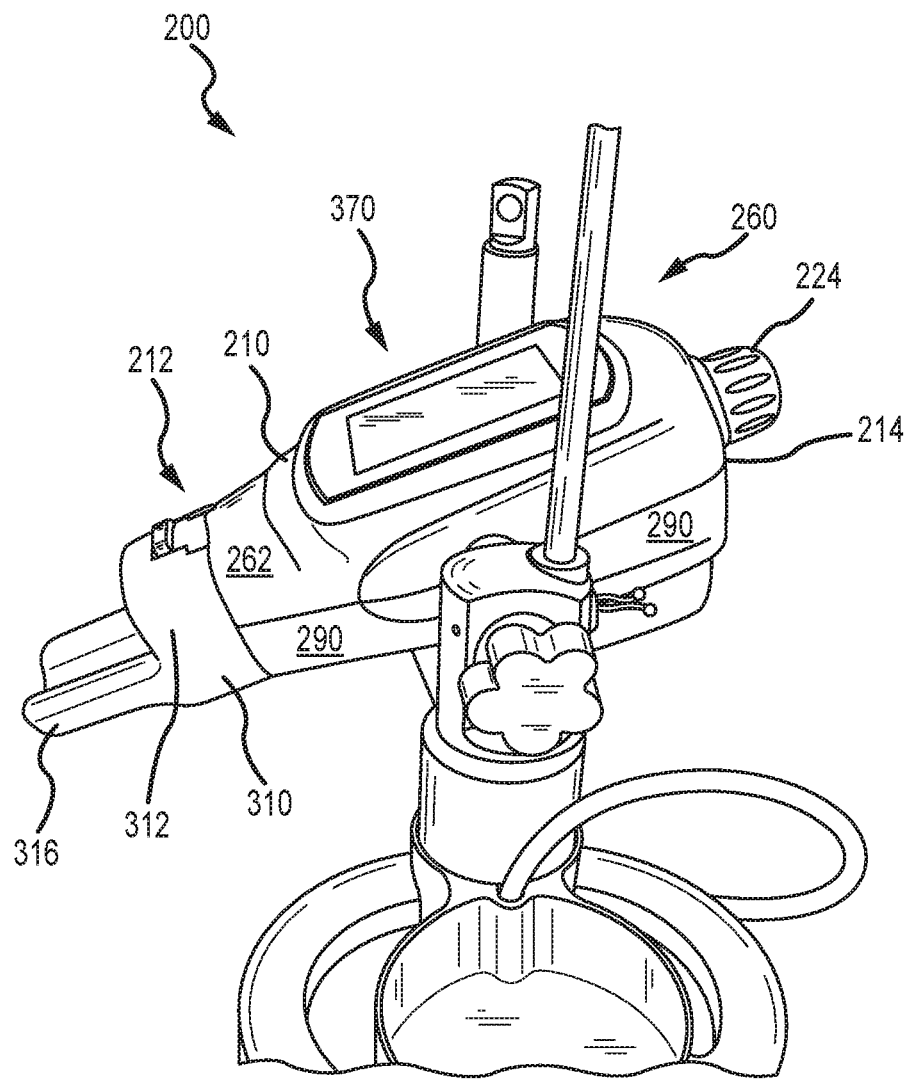
FIG. 3C is a perspective view of the top and the opposite side of the single-head power injector of FIG. 3A, and with its powerhead being in a tilted down orientation.
Figure 3D:
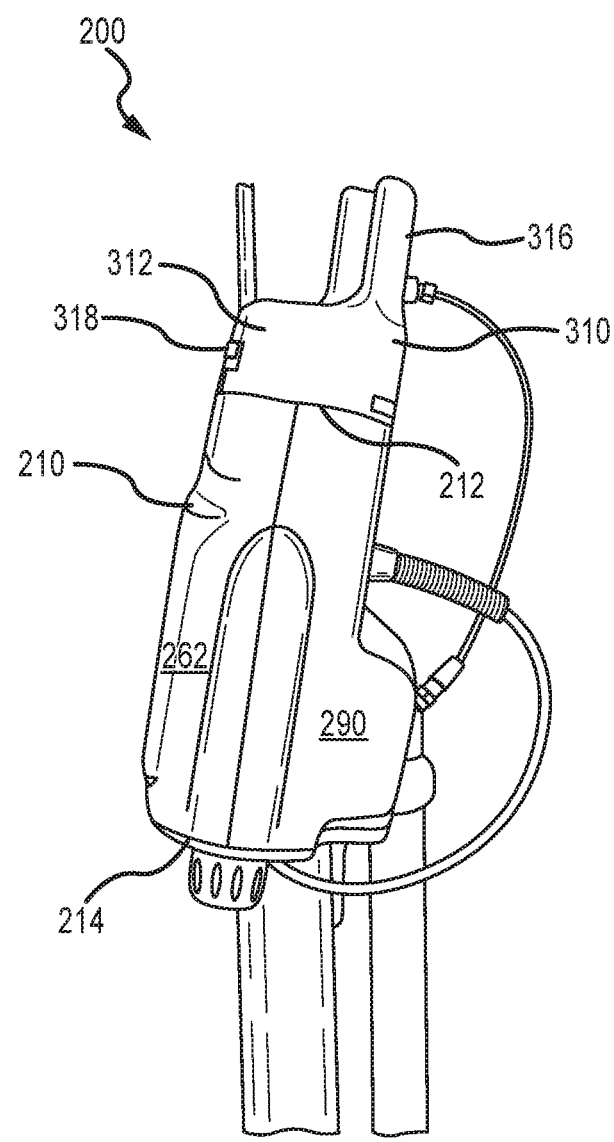
FIG. 3D is a perspective view of one side of the single-head power injector of FIG. 3A, and with its powerhead being in a tilted up orientation.
Figure 3E:
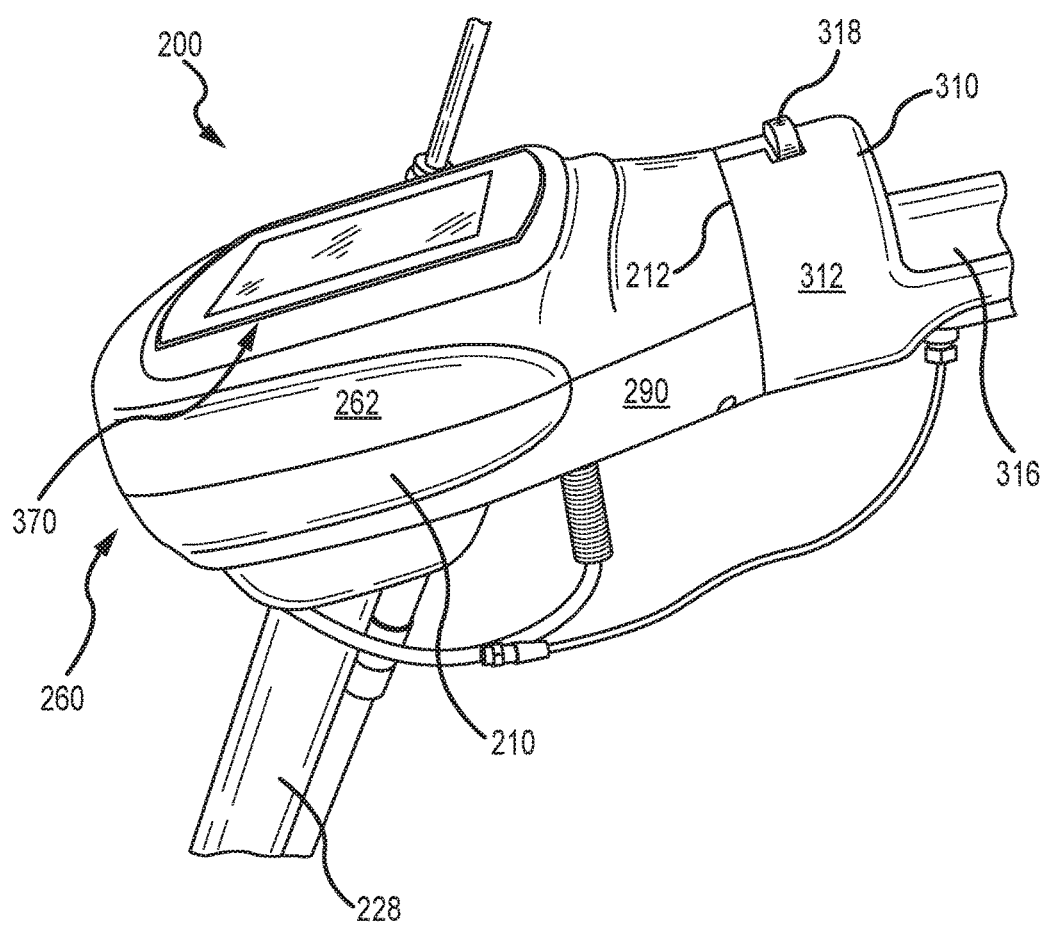
FIG. 3E is a perspective view of the top and one side of single-head power injector of FIG. 3A, and with its powerhead being in a tilted up orientation.
Figure 3F:
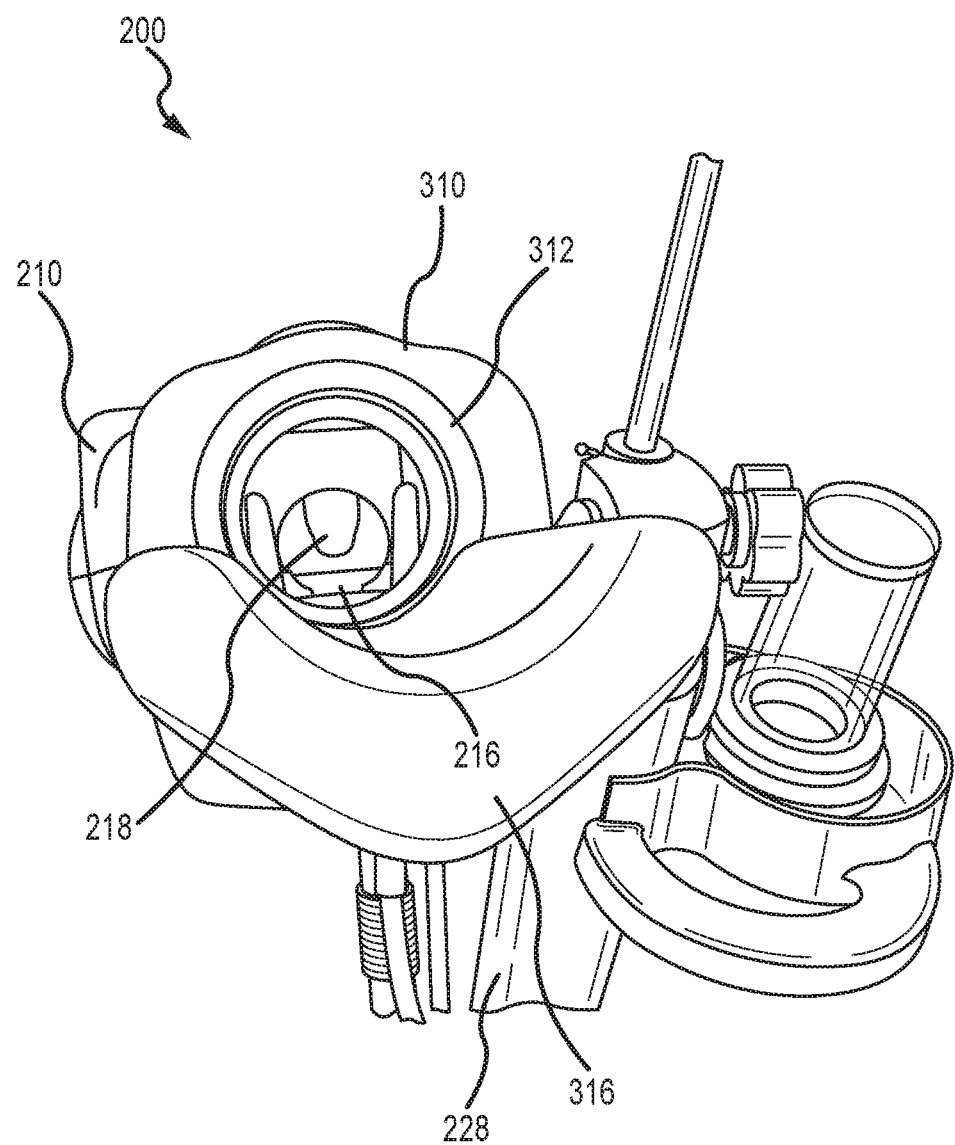
FIG. 3F is a perspective view of the front of the single-head power injector of FIG. 3A, and with its powerhead being in a tilted up orientation.

The powerhead 210 is mounted on a pole 228 in the illustrated embodiment, although the powerhead 210 could be mounted on a variety of other structures (e.g., an arm or arm assembly that extends from a wall, ceiling, or other supporting structure). The powerhead 210 is movable at least generally about a pivot 226 in either direction, and may be locked in the desired orientation in any appropriate manner (e.g., by a hand-activated clamping mechanism). FIGS. 3A-3C illustrate representative positions for the powerhead 210 when injecting fluid into a patient (where the front end 212 of the powerhead 210 is disposed at a lower elevation than the rear end 214 of the powerhead 210; a "tilted down" orientation for the powerhead 210) from a syringe that is installed on the powerhead 210 via the faceplate 310 and tubing that extends from this syringe to the patient. FIGS. 3D-3F illustrate representative positions in which the powerhead 210 may be disposed when loading fluid into a syringe that is installed on the powerhead 210 via the faceplate 310 (where the front end 212 of the powerhead 210 is disposed at a higher elevation than the rear end 214 of the powerhead 210; a "tilted down" position for the powerhead 210).

A front plate 230 is appropriately attached to the front end 212 of the powerhead 210 and is illustrated in FIGS. 4A-4E. A ram aperture 232 extends through the front plate 230, intersects a base or base surface 233 thereof (e.g., a flat surface that may be disposed at least generally perpendicular to the axis along which the drive ram 216 moves), and is aligned with the syringe aperture 314 through the faceplate 310 when installed on the powerhead 210. The drive ram 216 may move through this ram aperture 232 (and through the syringe aperture 314 of the faceplate 310) during operation of the motor or manual operation of the knob 224 by an operator. A faceplate mounting 234 protrudes from the base 233 and detachably receives the faceplate 310. The faceplate 310 may be moved within a plane that is at least generally perpendicular to the axis along which the drive ram 216 moves, both to install the faceplate 310 on the front plate 230 (e.g., via downward movement of the faceplate 310) and to remove the faceplate 310 from the front plate 230 (e.g., via upward movement of the faceplate 310).

The faceplate mounting 234 includes an arcuate face or surface 236 that is disposed at least generally at the lower extreme of the ram aperture 232 through the front plate 230. The arcuate face 234 may be characterized as extending away from the base 233 of the front plate 230 (e.g., the arcuate face 234 may be characterized as a ledge). One embodiment has the arcuate face 236 at least generally following an arcuate segment of the ram aperture 232 (e.g., less that 180°), including where the arcuate face 236 is positioned immediately adjacent to a perimeter portion of the ram aperture 232. The arcuate face 236 may be oriented parallel to the axis along which the drive ram 216 moves.

Figure 4A:
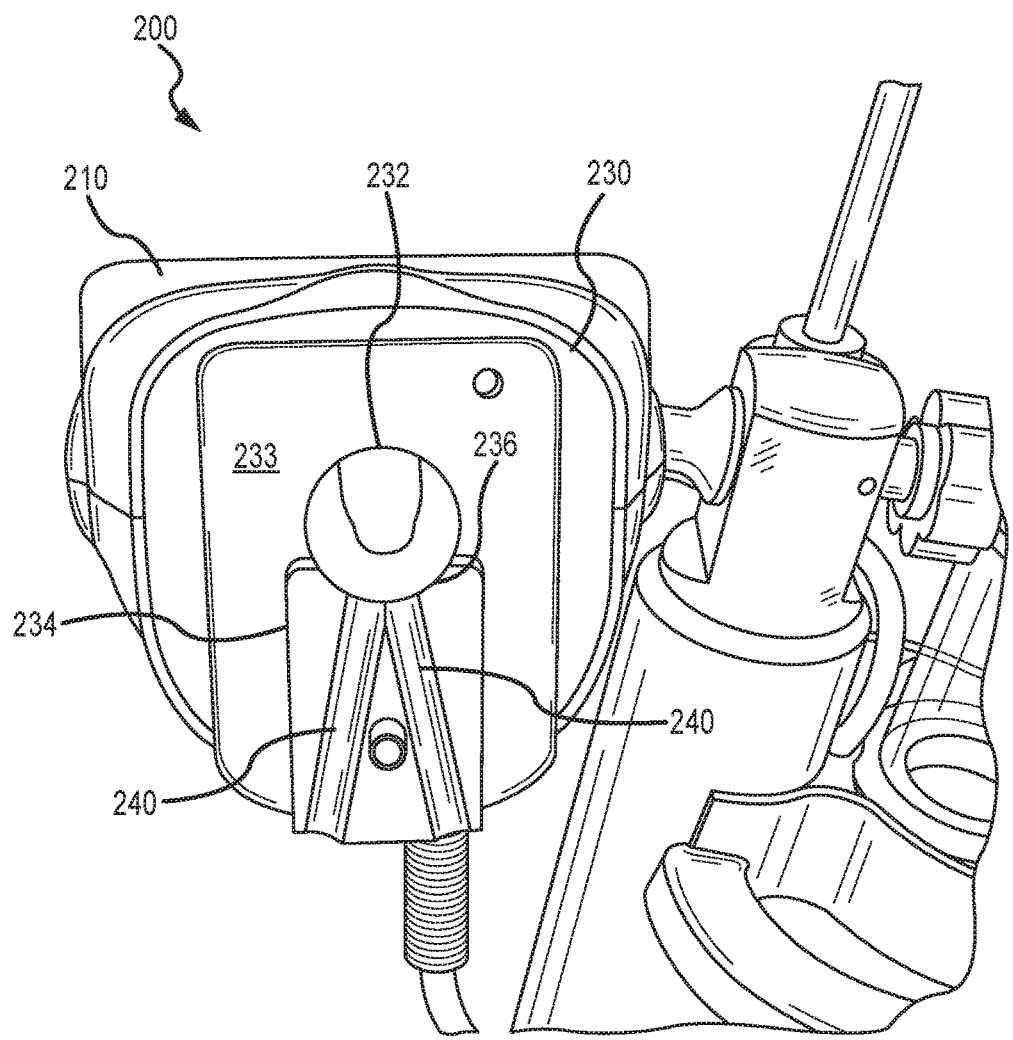
FIG. 4A is a perspective view of a front plate that is installed on the front end of the powerhead for the single-head power injector of FIG. 3A, and with a faceplate having been removed.
Figure 4B:
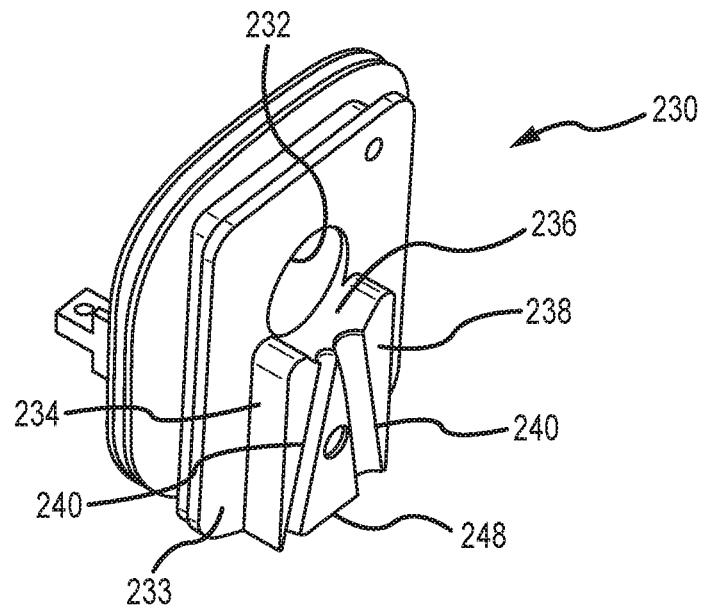
FIG. 4B is a perspective view of a front side of the front plate shown in FIG. 4A.
Figure 4C:
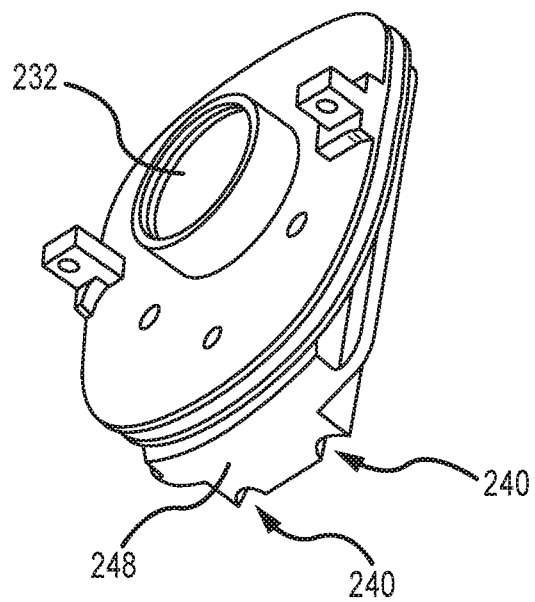
FIG. 4C is a perspective view of a back side of the front plate shown in FIG. 4A.
Figure 4D:
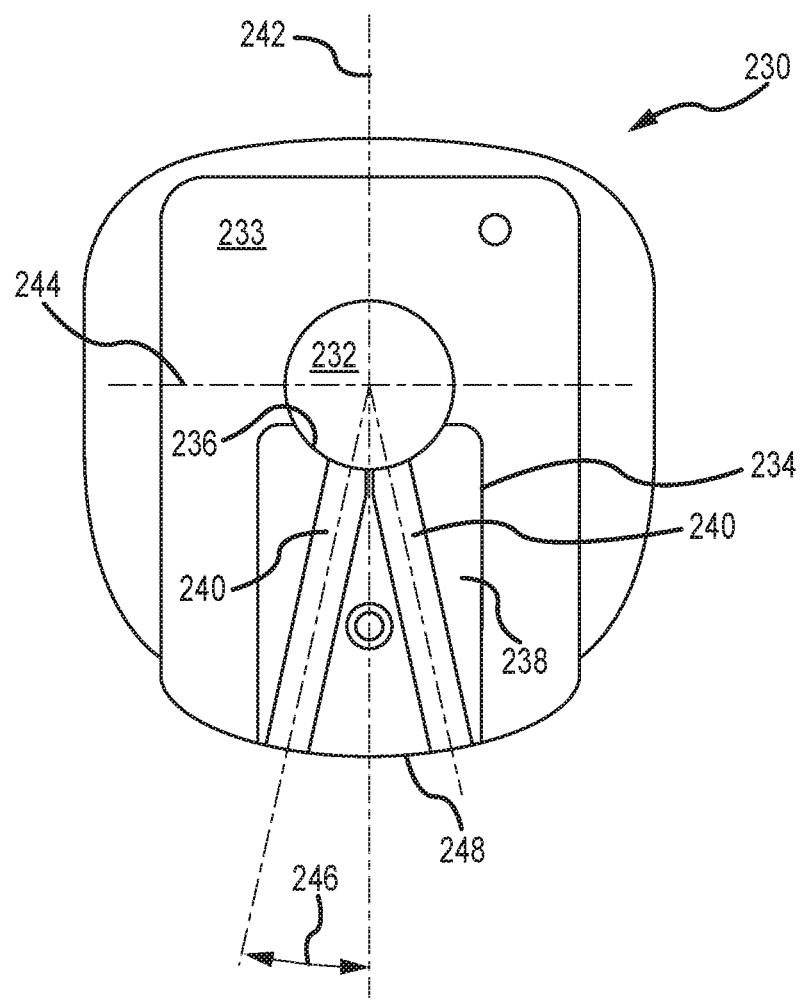
FIG. 4D is a plan view of the front side of the front plate shown in FIG. 4A.
Figure 4E:
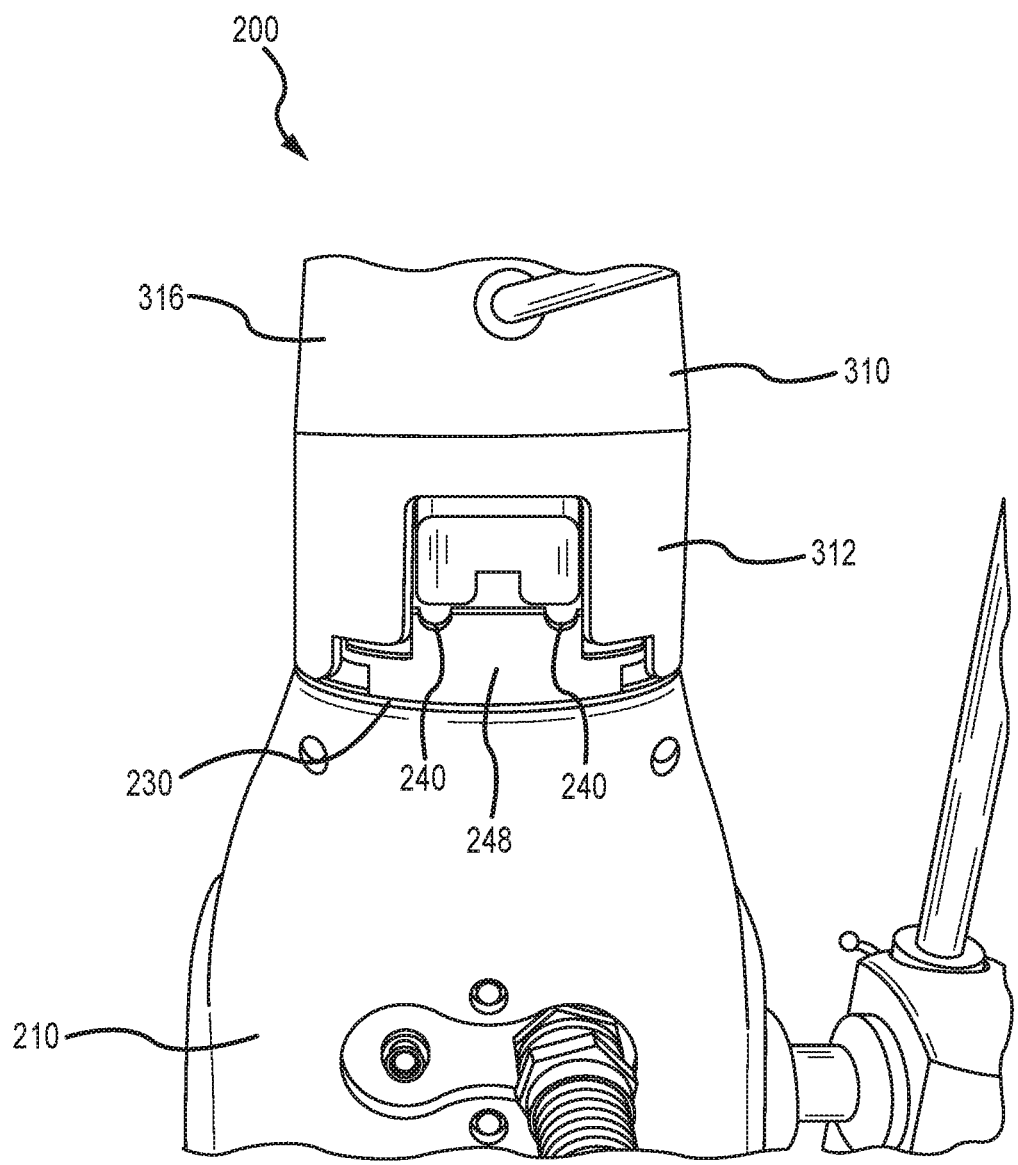
FIG. 4E is a perspective view of the bottom of the powerhead for the single-head power injector of FIG. 3A but with the faceplate being installed, and illustrating a bottom of the front plate shown in FIG. 4A.

The faceplate mounting 234 further includes a front face 238. A plurality of drainage channels 240 are formed in the front face 238 and extend from the arcuate face 236 to a lower end 248 of faceplate mounting 234. In the illustrated embodiment, there are two drainage channels 240 that are oriented as the mirror image of one another. A first reference axis 242 may be characterized as extending from a top of the powerhead 210 to a bottom of the powerhead 210, while a second reference axis 244 may be characterized as extending from one side of the powerhead 210 to an opposite side of the powerhead 210, all as shown in FIG. 4D and where the first reference axis 242 is orthogonal to the second reference axis 244. The first reference axis 242 and the second reference axis 244 may intersect at a point that coincides with the axis along which the drive ram 216 moves, and the drainage channels 240 may be symmetrically disposed related to these axes 242, 244. Each drainage channel 240 diverges away from the first reference axis 242 in proceeding from the arcuate face 236 of the faceplate mounting 234 (at the ram aperture 232) to the oppositely disposed lower end 248 of the faceplate mounting 234. In one embodiment, an included angle 246 between each drainage channel 240 and the first reference axis 242 is at least generally about 12.5 degrees. Other magnitudes for each included angle 246 may be utilized.

Fluid that leaks out of a syringe installed on the powerhead 210 via the faceplate 310 may collect on the arcuate surface 236 (most typically when the powerhead 210 is disposed in a "tilted up" orientation while fluid is being loaded into a syringe and/or while a purging operation (e.g., air removal) is being executed, all with the syringe having been previously installed on the powerhead 210 (e.g., FIGS. 3D and 3E)), may be directed into the drainage channels 240, and may flow through these drainage channels 240 for discharge out the bottom of the powerhead 210 (e.g., onto the floor). The drainage channels 240 may be characterized as directing contrast media away from the interior of the powerhead 210, which is desirable in a number of respects. Contrast media that has leaked out of a syringe installed on the powerhead 210 through the faceplate 310 could enter the interior of the powerhead 210 through the ram aperture 232 (or more typically through a cover assembly 260, addressed below), which could adversely impact performance of one or more components of the power injector 200. Moreover, contrast media that has leaked out of a syringe installed on the powerhead 210 through the faceplate 310 and that has collected between the faceplate 310 and the front plate 230 of the powerhead 210 could crystallize (e.g., increase the difficulty of cleaning the powerhead 210/faceplate 310; impacting the ability to smoothly disconnect the faceplate 310 from the front plate 230 of the powerhead 210).

Figure 5A:
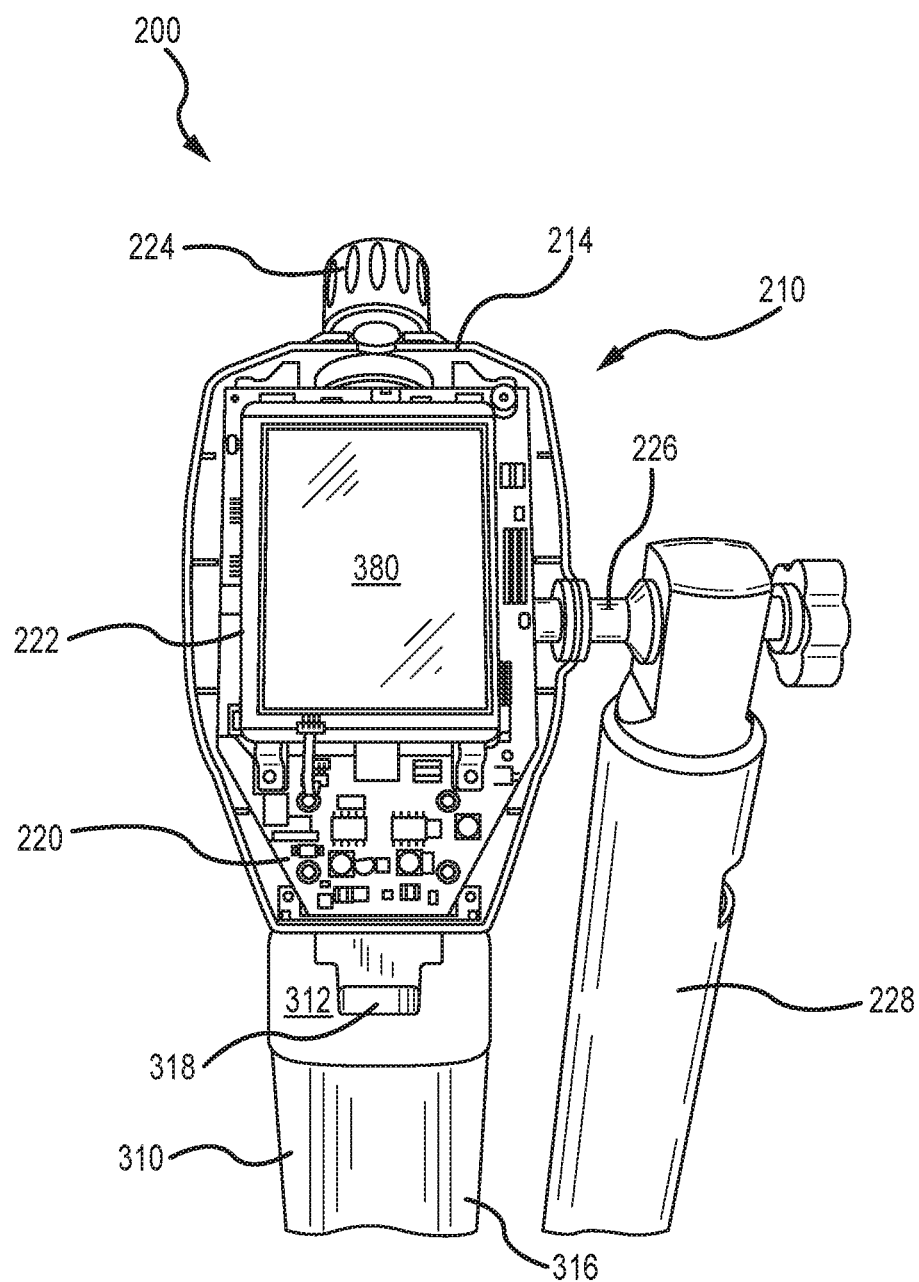
FIG. 5A is a perspective view of the top of powerhead for the single-head power injector of FIG. 3A, with a top cover and a bezel of the power injector having been removed to illustrate a touch screen display.
Figure 5B:
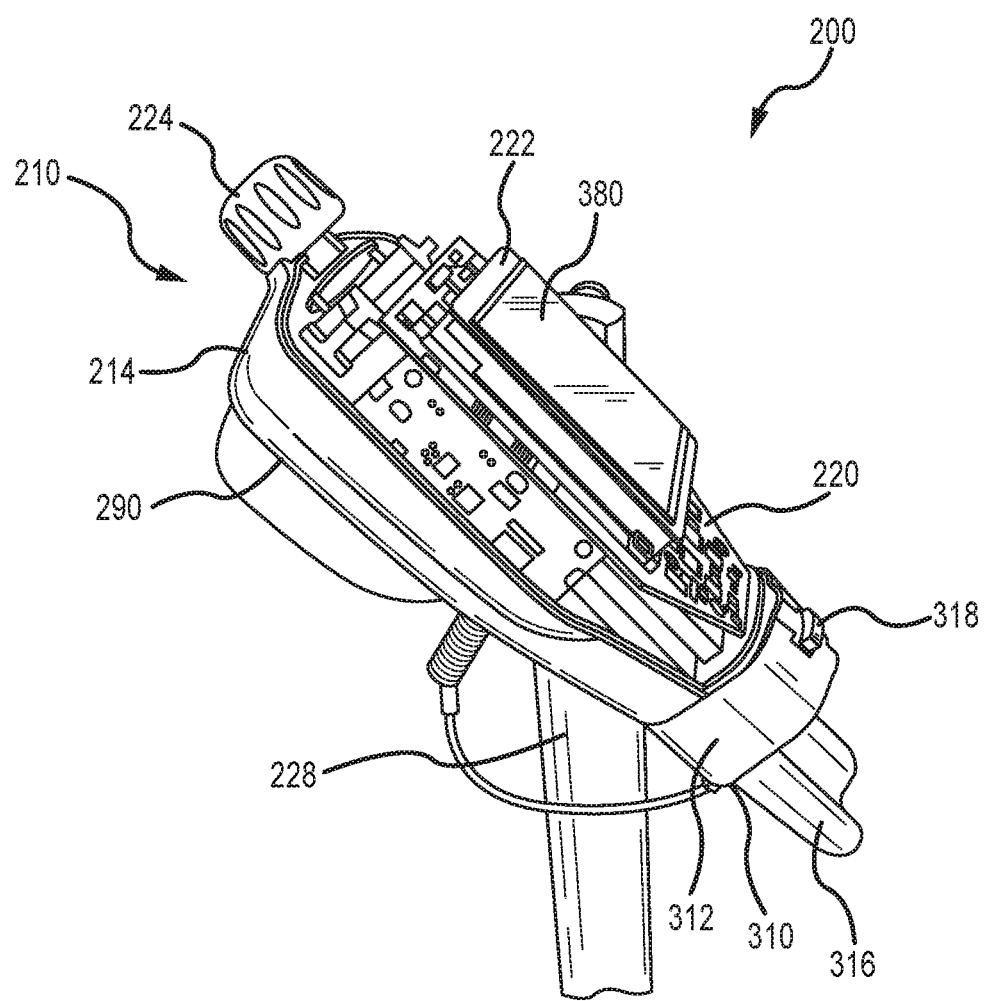
FIG. 5B is a perspective view of the top and one side of the powerhead for the single-head power injector of FIG. 3A, with the top cover and bezel having been removed to illustrate the touch screen display.
Figure 5C:
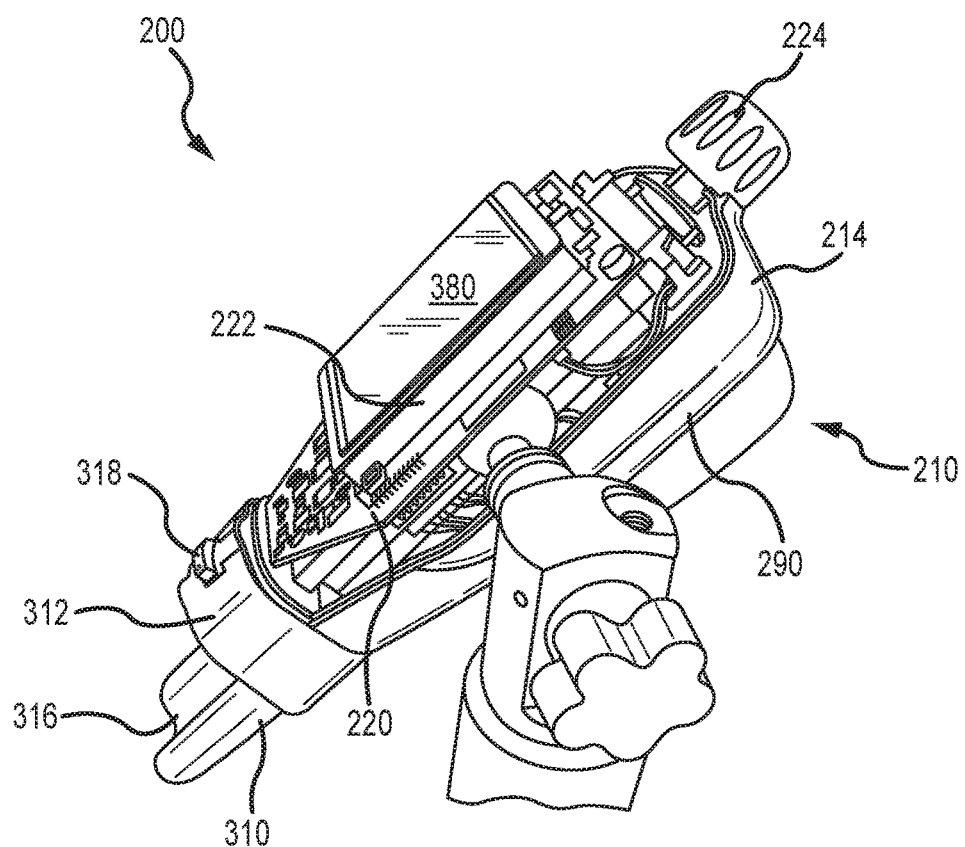
FIG. 5C is a perspective view of the top and the other side of the powerhead for the single-head power injector of FIG. 3A, with the top cover and bezel having been removed to illustrate the touch screen display.

A touch screen display 380 is incorporated by the powerhead 210, accommodates displaying information to an operator of the power injector 200, and further accommodates provision of operator input to the power injector 200 (e.g., by touching a relevant portion of the touch screen display 380). As shown in FIGS. 5A-5C, the powerhead 210 includes a printed circuit board 220 for controlling operation of the power injector 200. The touch screen display 380 and the printed circuit board 220 are operatively interconnected or coupled in an appropriate manner. A display mounting bracket 222 may be used to secure the touch screen display 380 relative to the printed circuit board 220.

Figure 6A:
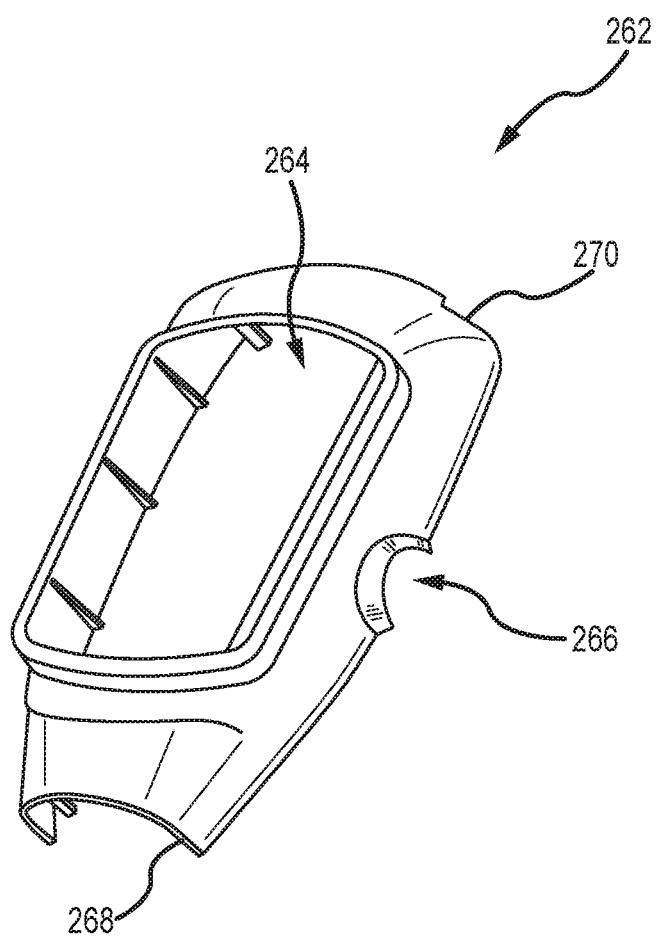
FIG. 6A is a perspective view of the top side of a top cover for the single-head power injector of FIG. 3A.
Figure 6B:
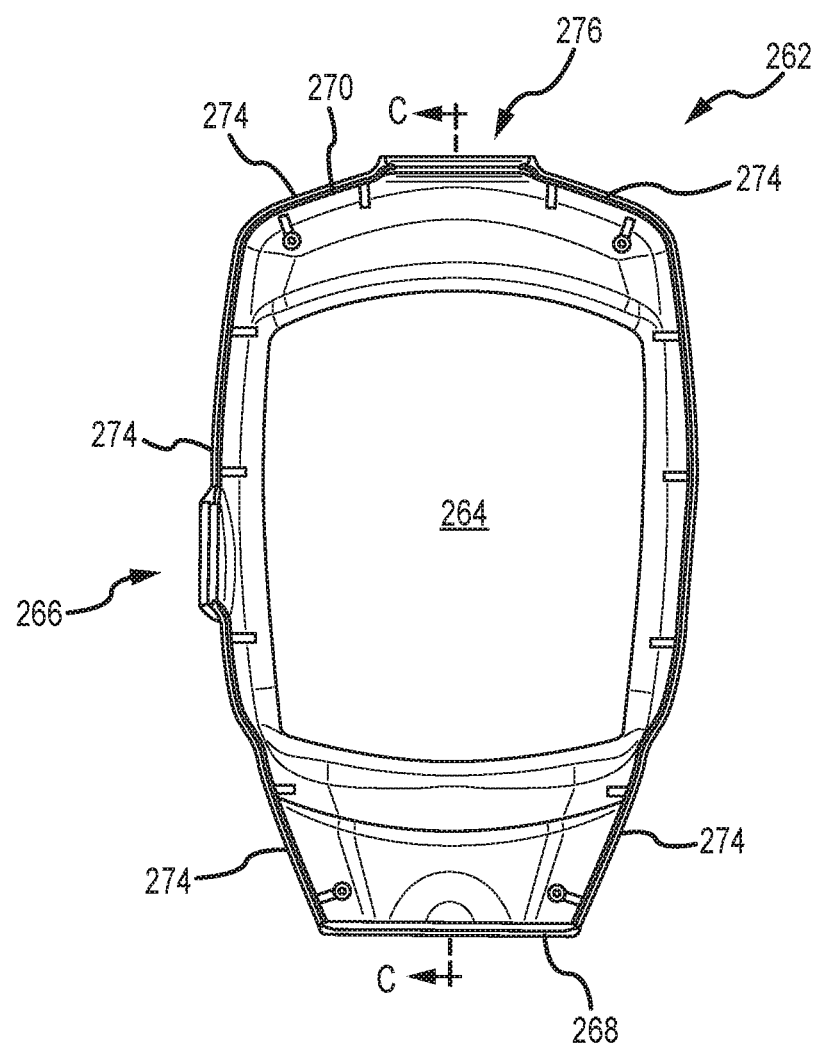
FIG. 6B is a bottom plan view of the top cover shown in FIG. 6A.
Figure 6C:
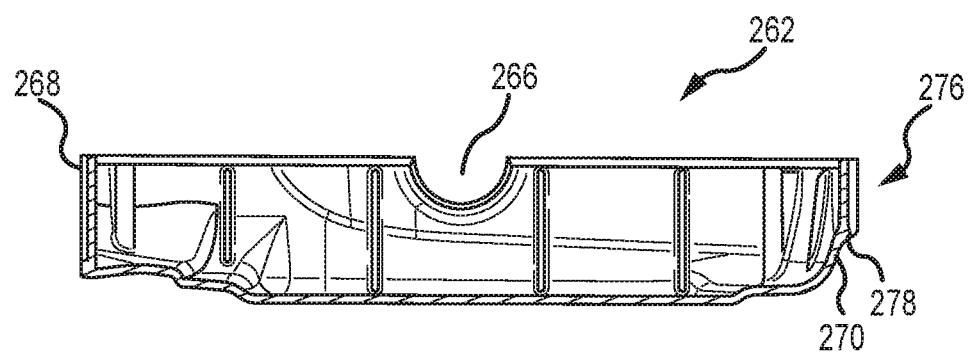
FIG. 6C is a cross-sectional view of the top cover shown in FIG. 6B, and taken along line C-C.
Figure 6D:
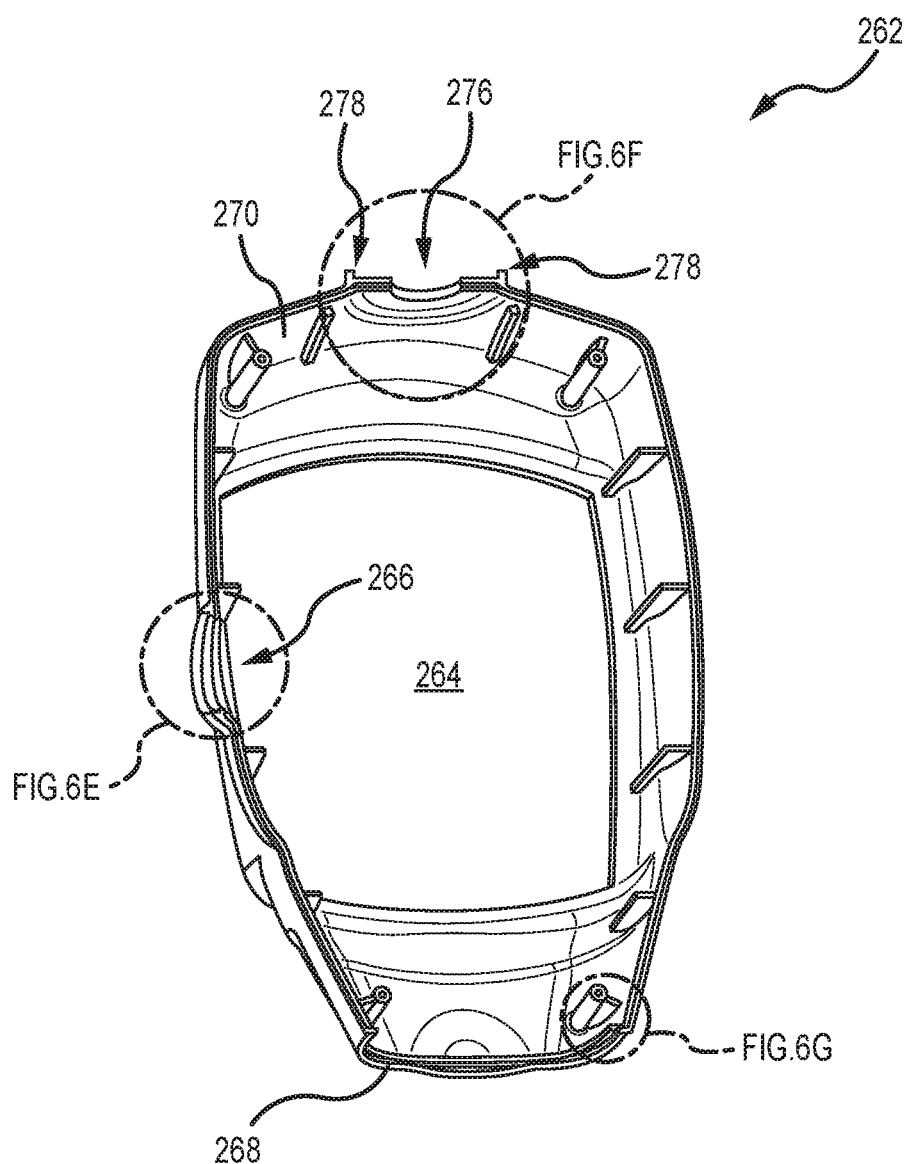
FIG. 6D is a perspective view of the bottom or underside for the top cover shown in FIG. 6A.
Figure 6F:
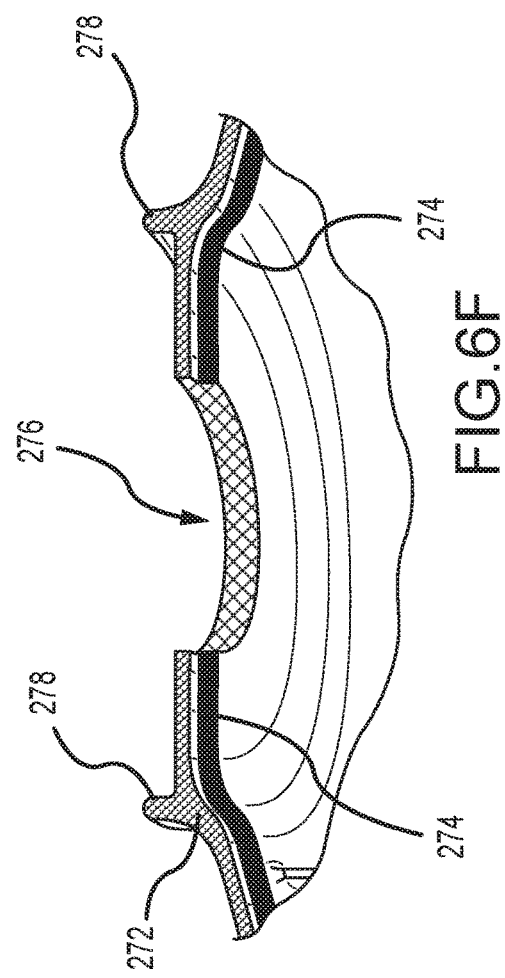
FIG. 6F is an enlarged view of the region 6F for the top cover presented in FIG. 6D.
Figure 6G:
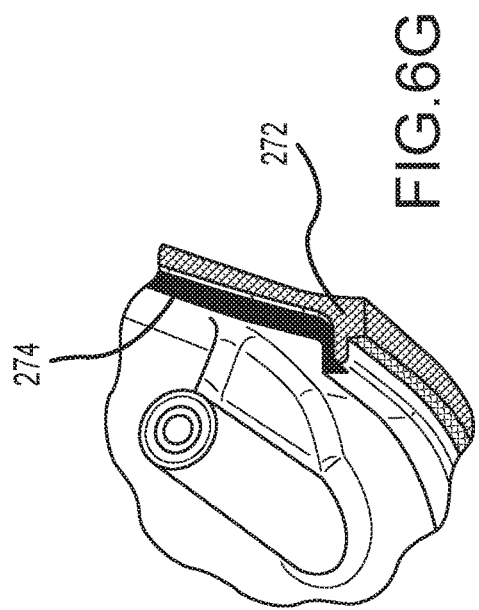
FIG. 6G is an enlarged view of the region 6G for the top cover presented in FIG. 6D.
Figure 6E:
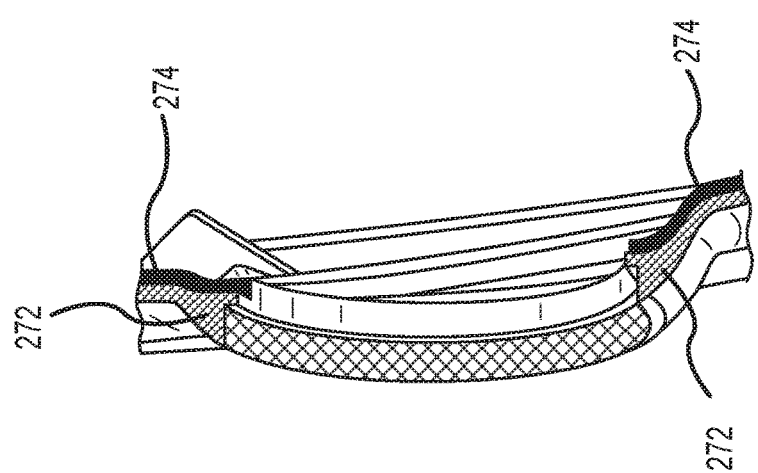
FIG. 6E is an enlarged view of the region 6E for the top cover presented in FIG. 6D.
Figure 7:
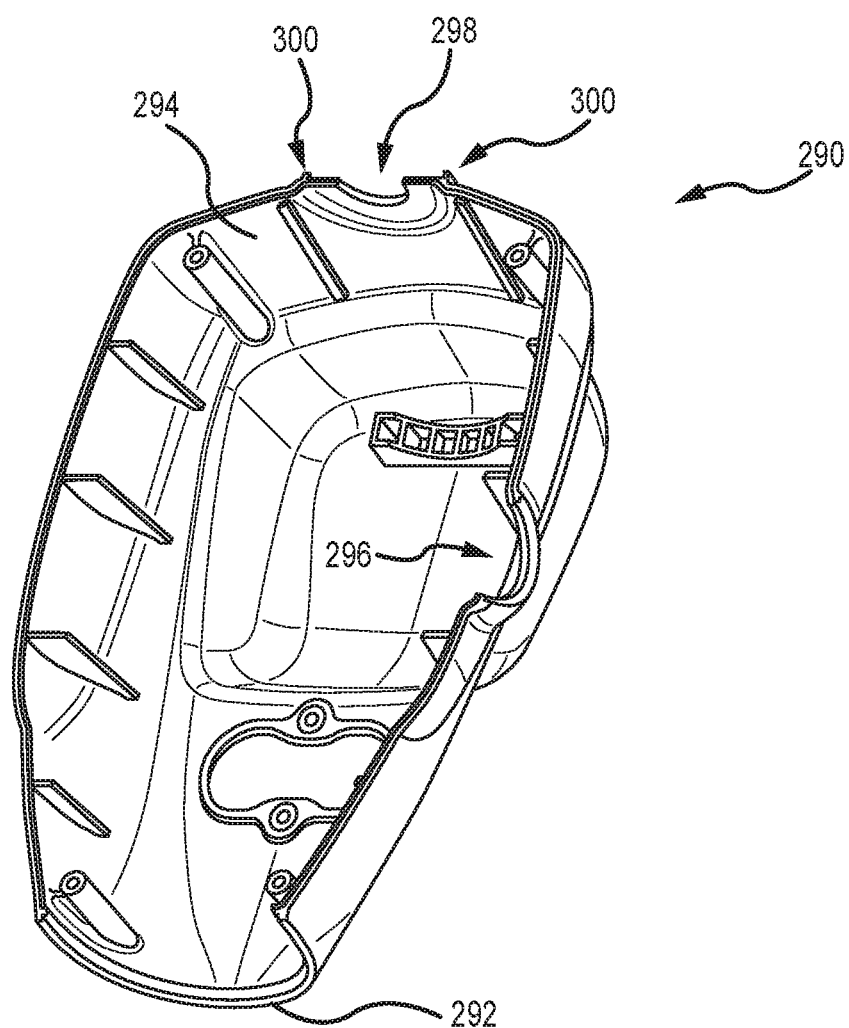
FIG. 7 is a perspective view of an interior of a bottom cover for the single-head power injector of FIG. 3A.

A cover assembly 260 at least generally defines a housing for the powerhead 210. Components of the cover assembly 260 include a top cover 262 (FIGS. 6A-6G) and a bottom cover 290 (FIG. 7). The top cover 262 extends between a front end 268 (which receives a corresponding portion of the front plate 230) and a rear wall 270, and includes a display aperture 264 on a top side thereof for providing operator access to the touch screen display 380. A pivot aperture 266 is formed on one side of the top cover 262 and defines part of the aperture through which the noted pivot 226 for the powerhead 210 extends. A knob aperture 276 is formed in the rear wall 270 of the top cover 262 and defines part of the aperture through which the knob 224 extends (the knob 224 again being for manually advancing the drive ram 216 in either direction along an axis). An upper rim 278 protrudes from the rear wall 270 of the top cover 262, and is disposed about this knob aperture 276.

The cover assembly 260, including the top cover 262, includes a number of features to manage "spilled" contrast media. One is that the top cover 262 incorporates a form-in-place or FIP gasket 274. This FIP gasket 274 is secured to the top cover 262 (e.g., adhered) and engages the bottom cover 290 throughout the entirety of the interface between the top cover 262 and the bottom cover 290. The FIP gasket 274 extends about the entire perimeter of the top cover 262, except for the wall of the top cover 262 that defines the pivot aperture 266 (which does not interface with the bottom cover 290, and as shown in FIG. 6E), except for the wall of the top cover 262 that defines the knob aperture 276 (which also does not interface with the bottom cover 290, and as shown in FIG. 6F), and where the top cover 262 interfaces with the front plate 230 (FIG. 6G). The FIP gasket 274 should stay secured to the top cover 262 when the cover assembly 260 is disassembled (e.g., when the top cover 262 is removed from the bottom cover 290), and which should facilitate reassembly of the cover assembly 260 in relation to maintaining a desired seal between the top cover 262 and the bottom cover 290 (the potential should be reduced of the FIP gasket 274 being displaced when the top cover 262 is assembled with the bottom cover 290, where displacement of the FIP gasket 274 could adversely impact the seal between the top cover 262 and the bottom cover 290).

The bottom cover 290 extends between a front end 292 (which receives a corresponding portion of the front plate 230) and a rear wall 294. A pivot aperture 296 is formed on one side of the bottom cover 290 and defines part of the aperture through which the pivot 226 for the powerhead 210 extends. A knob aperture 298 is formed in the rear wall 294 of the bottom cover 290 and defines part of the aperture through which the knob 224 (for manually advancing the drive ram 216) extends. A lower rim 300 protrudes from the rear wall 294 of the bottom cover 290, and is disposed about this knob aperture 298.

A lower portion of the top cover 262 extends over an upper portion of the bottom cover 290 when assembled—the top cover 262 overlaps the bottom cover 290 in the illustrated embodiment and when the top cover 262 and bottom cover 290 are assembled. In this regard, the FIP gasket 274 is recessed relative to a lower end 272 of the top cover 262. As such, the FIP gasket 274 may engage the two sidewalls of the bottom cover 290 and the rear wall 294 of the bottom cover 290, and reduces the potential of contrast media (or other fluids) entering the interior of the powerhead 210 between the top cover 262 and the bottom cover 290.

Figure 8A:
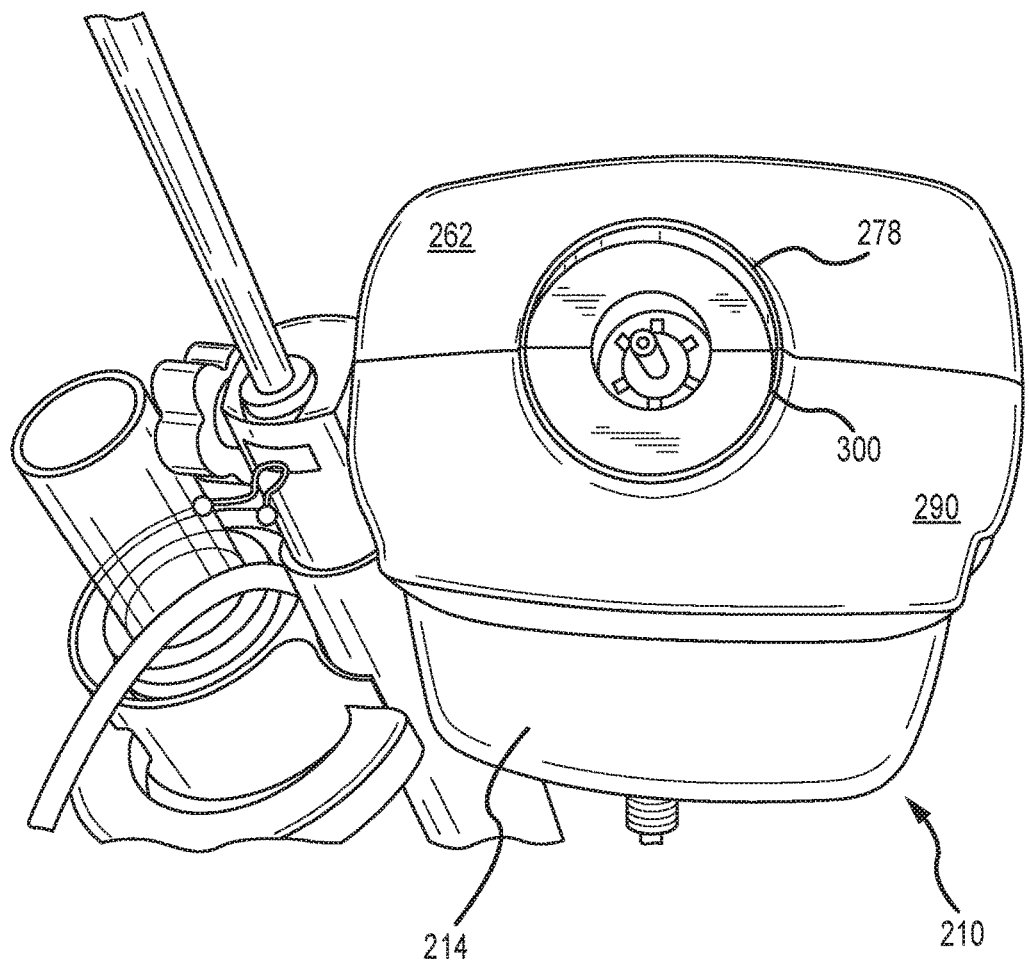
FIG. 8A is a perspective view of a rear end of the powerhead for the single-head power injector of FIG. 3A, with a knob for manually controlling a drive ram having been removed to illustrate an annular fluid-control rim that is disposed about an aperture in a cover assembly for this knob.
Figure 8B:
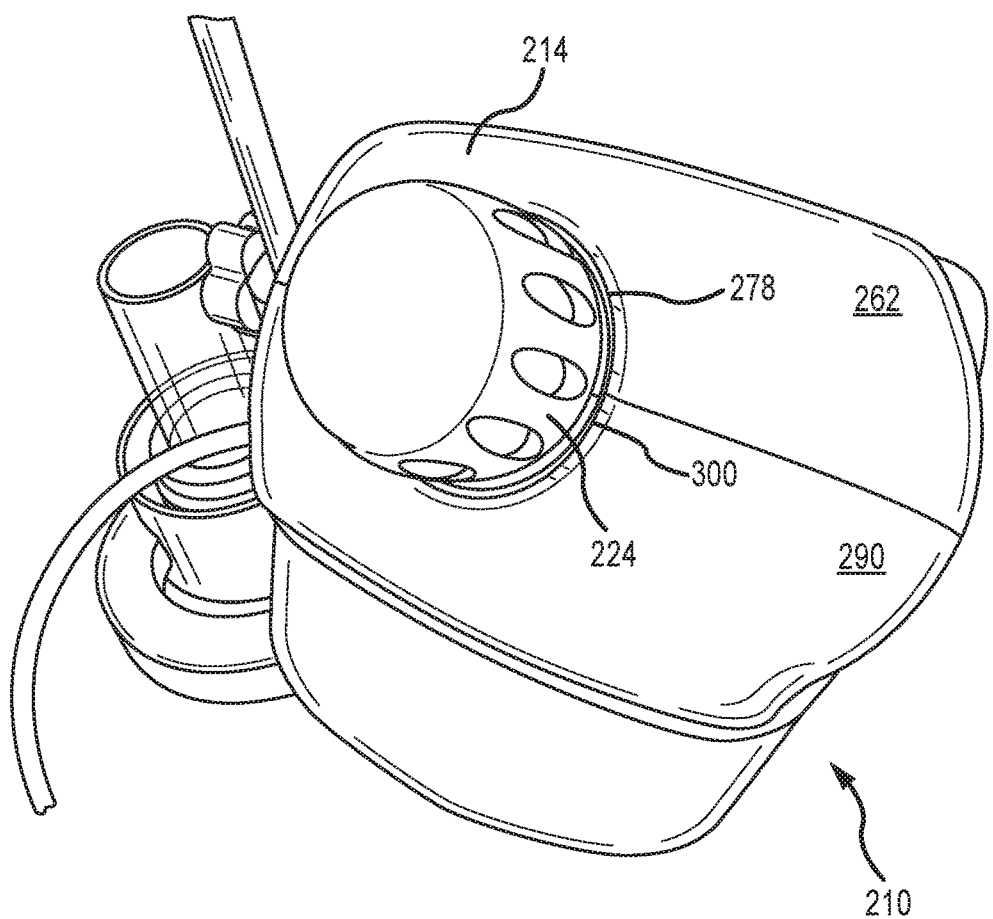
FIGS. 8B and 8C are different perspective views of the rear end of the powerhead for the single-head power injector of FIG. 3A and with the knob being installed.
Figure 8C:
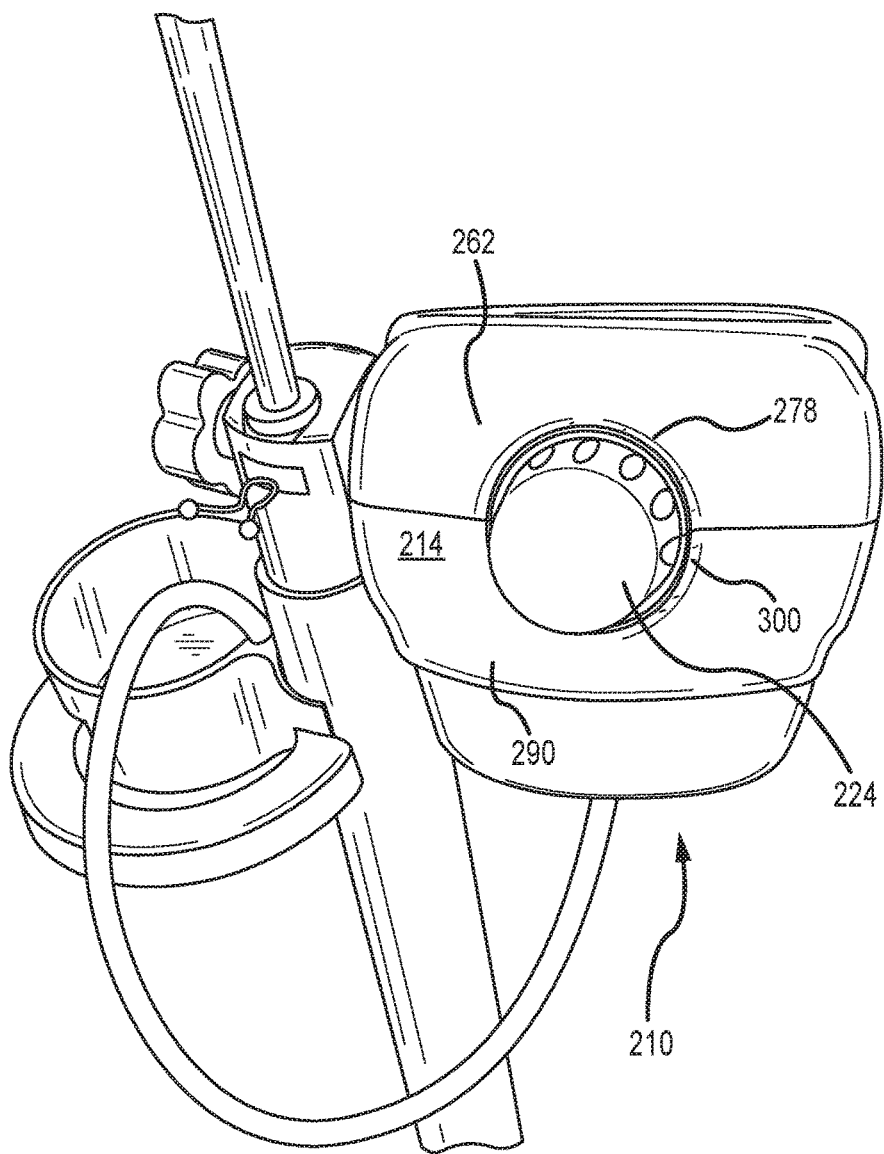

FIGS. 8A-8C show the top cover 262 being assembled with the bottom cover 290 to provide another contrast management feature. Generally, the upper rim 278 of the top cover 262 and the lower rim 300 of the bottom cover 290 cooperate to define an annular wall or protrusion that extends about the entire circumference of the aperture in the cover assembly 260 (collectively defined by the knob aperture 276 of the top cover 262 and the knob aperture 298 of the bottom cover 290) through which the knob 224 extends (again, where the knob 224 may be manually rotated by an operator to advance the drive ram 216 relative to the powerhead 210 in the desired direction along the associated axis). The upper rim 278 of the top cover 262 and the lower rim 300 of the bottom cover 290 should reduce the potential of contrast media (or other fluids) entering the interior of the powerhead 210 via the aperture in the cover assembly 260 through which the knob 224 extends.

Figure 9B:
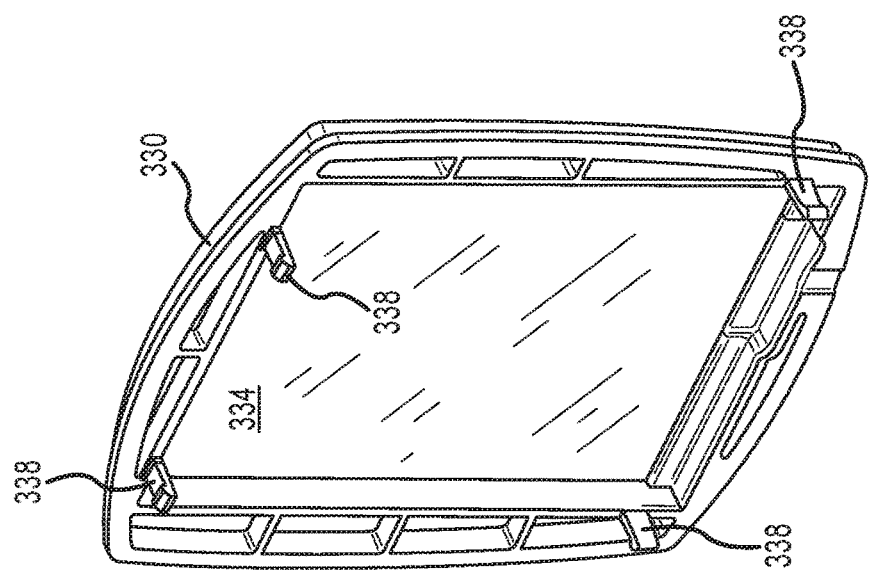
FIG. 9B is a perspective view of a back side of the bezel shown in FIG. 9A.
Figure 9A:
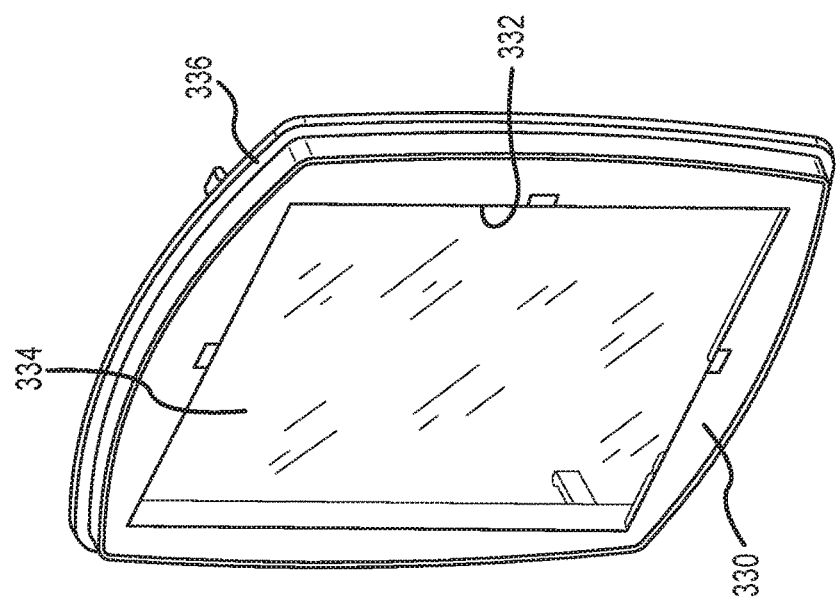
FIG. 9A is a perspective view of a front side of a bezel used by the single-head power injector of FIG. 3A.

The power injector 200 includes a touch screen display 380 and as noted above. Instead of the top cover 262 including an integral and transparent overlay that coincides with the display aperture 264, the power injector 200 uses a display assembly 370 that includes the touch screen display 380 and a separate bezel 330. Referring now to FIGS. 9A-9B, the bezel 330 includes an aperture 332 and a transparent overlay 334 that coincides with this aperture 332. The perimeter of the bezel 330 includes a gasket flange 336. The back of the bezel 330 includes a plurality of mounting tabs 338 that may be used to detachably secure the bezel 330 to the touch screen display 380 and/or its corresponding display mounting bracket 222 (discussed above).

Figure 11A:
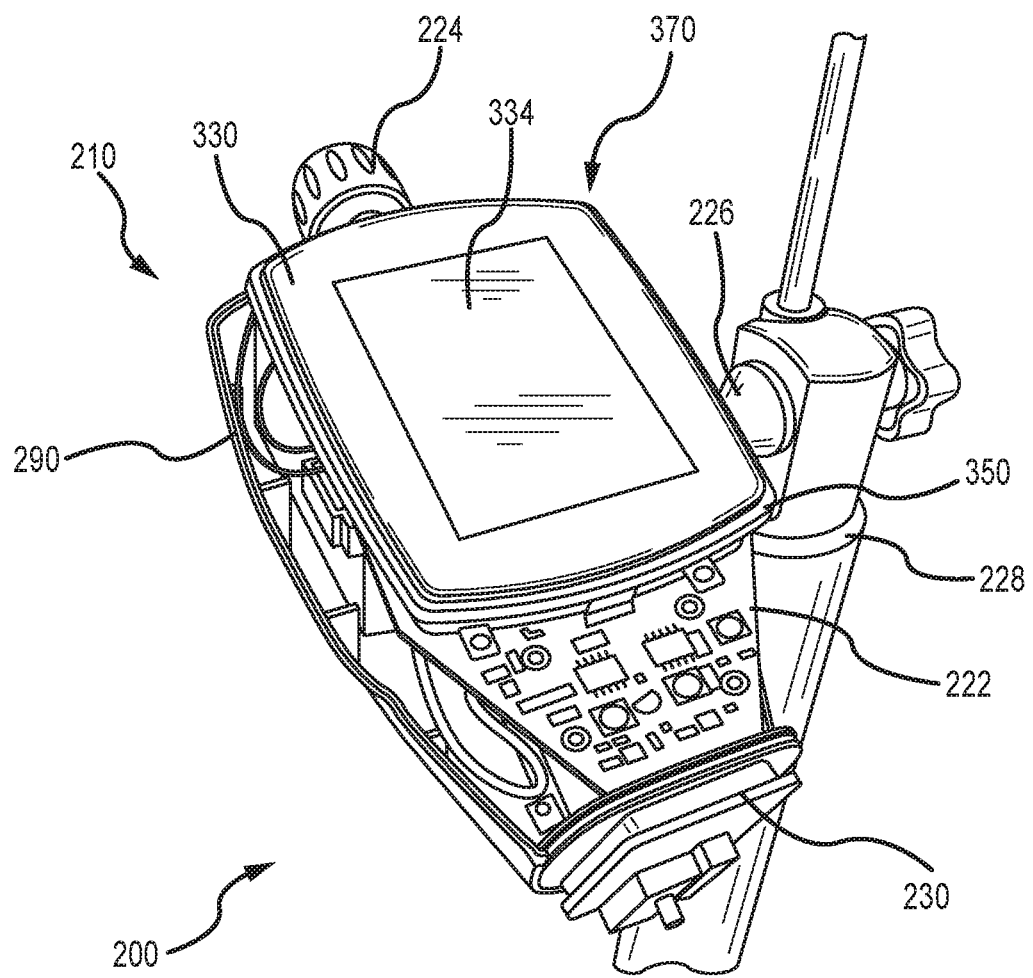
FIGS. 11A and 11B are perspective views of the powerhead for the single-head power injector of FIG. 3A, with the top cover having been removed to illustrate a display assembly.
Figure 11B:
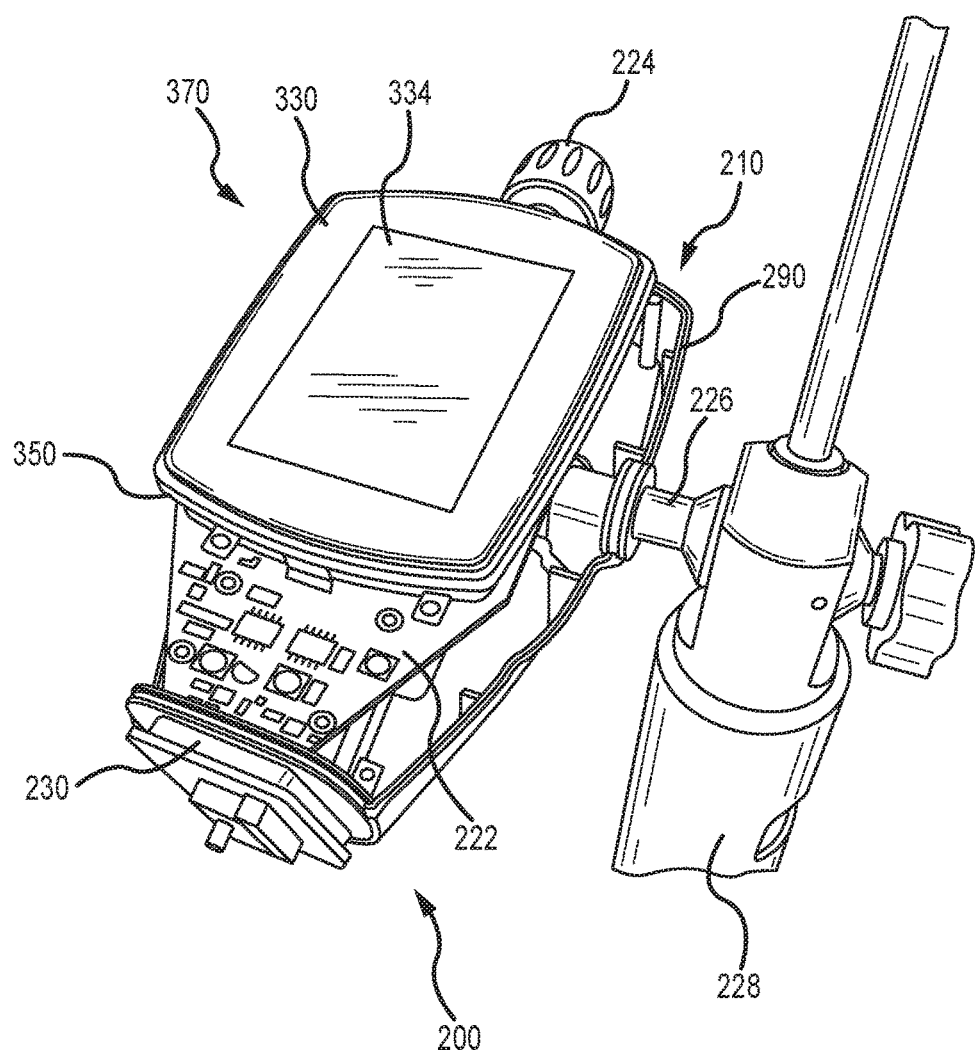

A seal is provided between the bezel 330 and the top cover 262 when these components are assembled. Such a seal is illustrated in FIGS. 10A-10C and is in the form of a bezel gasket 350. The bezel gasket 350 is an annular structure so as to extend about the entire perimeter of the bezel 330 when installed thereon. As shown in FIG. 10C, the bezel gasket 350 includes a back-section 352, a mid-section 354 and a front-section 356. A bezel flange cavity 358 is defined between the back-section 352 and the mid-section 354. The gasket flange 336 of the bezel 330 is received in this bezel flange cavity 358. A sealing cavity 360 is defined by the mid-section 354 and the front-section 356 (e.g., in the form of a cantilever). When the top cover 262 is positioned over the bezel 330, the front section 356 of the bezel gasket 350 is engaged by the top cover 262 to provide a desired seal between the top cover 262 and the bezel 330. For instance, the front section 356 of the bezel gasket 350 may deflect through free space and into engagement with the bezel 330 when the top cover 262 is installed over the bezel 330 and comes into contact with the bezel gasket 350. FIGS. 11A-11B illustrate the bezel 330 installed on the touchscreen display 380, which is in turn installed on the powerhead 220 in the above-noted matter.

The overlay 334 is not intended to be removed from the bezel 330. If the overlay 334 becomes scratched or otherwise obstructs viewing of the touch screen display 380, the top cover 262 may be removed from the powerhead 210 and the bezel 330 may be replaced. This is a more desirable configuration than the case where such an overlay is incorporated by a top cover.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

The invention claimed is:
1. A power injector comprising:
a first drive source;
a powerhead comprising a drive ram that is interconnected with said first drive source and that is movable along a reference axis in at least a first direction through operation of at least said first drive source, wherein said powerhead further comprises a front plate, and wherein said front plate comprises a ram aperture, aligned with said drive ram, and at least one drainage channel;
a syringe mount installed on said powerhead; and
a flowpath that extends from said ram aperture to an exterior of said power injector when a syringe is interconnected with said syringe mount, wherein said flowpath comprises said at least one drainage channel and with said at least one drainage channel extending to said exterior of said power injector.

2. The power injector of claim 1, wherein said at least one drainage channel comprises a first drainage channel with first and second ends that are spaced along a length dimension of said first drainage channel and with said length dimension corresponding with a direction of flow along said first drainage channel, wherein said first end of said first drainage channel is positioned closer to said reference axis than said second end of said first drainage channel, and wherein said second end of said first drainage channel is disposed at a lower elevation than said first end of said drainage channel when said reference axis is disposed in a horizontal orientation.

3. The power injector of claim 1, wherein said front plate comprises a face that is spaced from an end of said ram aperture along said reference axis, wherein said ram aperture and said face project in a common direction, and wherein said at least one drainage channel is formed on said face.

4. The power injector of claim 3, wherein said face comprises a first groove, wherein said at least one drainage channel comprises said first groove.

5. The power injector of claim 3, wherein said face is disposed within a plane that is at least generally perpendicular to said reference axis.

6. The power injector of claim 1, wherein said front plate further comprises a first surface and a front face, wherein said first surface and said front face are disposed in different orientations, wherein said first surface is disposed in proximity to said ram aperture and defines one portion of said flowpath, and wherein each said drainage channel is formed on said front face and defines a different portion of said flowpath.

7. The power injector of claim 6, wherein said first surface is arcuate.

8. The power injector of claim 6, wherein said first surface is disposed at least generally parallel with said reference axis along which said drive ram moves, and wherein said front face is disposed within a plane that is at least generally perpendicular to said reference axis.

9. The power injector of claim 6, wherein said first surface is positioned along only a portion of a perimeter of said ram aperture.

10. The power injector of claim 1, wherein each said drainage channel is an open, concave structure.

11. The power injector of claim 1, wherein each said drainage channel projects away from said powerhead.

12. The power injector of claim 1, wherein each said drainage channel projects in a direction in which said drive ram moves for a fluid discharge operation.

13. The power injector of claim 1, wherein said at least one drainage channel comprises first and second drainage channels.

14. The power injector of claim 13, wherein said first and second drainage channels are oriented as the mirror image of one another.

15. The power injector of claim 13, wherein said first and second drainage channels diverge away from one another proceeding away from both said reference axis and said ram aperture.

16. The power injector of claim 1, further comprising a cover assembly, wherein said cover assembly comprises a top cover detachably connected with a bottom cover, wherein said top cover comprises a form-in-place gasket that is anchored to said top cover and that seals against said bottom cover.

17. The power injector of claim 16, wherein said form-in-place gasket is adhered to said top cover.

18. The power injector of claim 16, wherein said form-in-place gasket engages said bottom cover throughout an entirety of an interface between said top cover and said bottom cover.

19. The power injector of claim 16, wherein said top cover comprises a lower end that defines a lower perimeter of said top cover, and wherein said form-in-place gasket is recessed relative to said lower end and is located within an interior of said top cover.

20. The power injector of claim 19, wherein an overlap exists between said top cover and said bottom cover, and wherein said form-in-place gasket is disposed within an entirety of said overlap.

21. The power injector of claim 16, wherein said cover assembly comprises a rear wall, an aperture extending through said rear wall, and an annular rim that protrudes from said rear wall and that is disposed about the entire circumference of said aperture.

22. The power injector of claim 21, further comprising:
a knob that is aligned with said aperture through said rear wall of said cover assembly and that is interconnected with said drive ram for manual movement of said drive ram through manual rotation of said knob.

23. The power injector of claim 21, wherein said annular rim protrudes at least about 0.125 inches beyond said rear wall.

24. The power injector of claim 16, wherein said powerhead further comprises:
a touch screen display; and
a bezel comprising an overlay disposed over said touch screen display, and a bezel gasket disposed about a perimeter of said bezel, wherein said top cover engages said bezel gasket.

25. The power injector of claim 24, further comprising:
a printed circuit board; and
a display mounting bracket maintained in a fixed position relative to said printed circuit board, wherein said bezel detachably engages at least one of said display mounting bracket or said touch screen display.

26. The power injector of claim 1, wherein said front plate further comprises a base surface and a protrusion that extends from said base surface, wherein said ram aperture intersects with and terminates at said base surface, wherein said protrusion comprises a front face that is spaced from said base surface in a dimension corresponding with said reference axis, wherein said protrusion further comprises a first surface that is disposed at a lower extreme of said ram aperture when said reference axis is in a horizontal orientation and that extends from said base surface to said front face, and wherein said at least one drainage channel is formed on said front face and intersects said first surface.

27. The power injector of claim 1, wherein when said reference axis is horizontally disposed and with a horizontal reference plane extending through said reference axis: 1) one part of said ram aperture is positioned above said horizontal reference plane and another part of said ram aperture is positioned below said horizontal reference plane; and 2) an entirety of each drainage channel, of said at least one drainage channel, is disposed below said reference plane.

28. A power injector comprising:
a first drive source;
a powerhead comprising a drive ram that is interconnected with said first drive source and that is movable along a reference axis in at least a first direction through operation of at least said first drive source, wherein said powerhead further comprises a front plate, wherein said front plate comprises a ram aperture, aligned with said drive ram, and at least one drainage channel, wherein said front plate further comprises a faceplate mounting, and wherein said at least one drainage channel is formed on said faceplate mounting; and
a syringe mount installed on said powerhead, wherein said syringe mount comprises a faceplate, wherein said faceplate detachably mounted to said faceplate mounting.

29. The power injector of claim 28, wherein said faceplate further comprises a syringe aperture aligned with said ram aperture, wherein a syringe is disposable within said syringe aperture, and wherein a syringe body of the syringe is maintainable in a fixed position relative to each of said faceplate and said powerhead.

30. The power injector of claim 28, wherein each said drainage channel is located between said front plate and said faceplate.

* * * * *